(12) United States Patent
Matsumoto

(10) Patent No.: US 7,514,667 B2
(45) Date of Patent: Apr. 7, 2009

(54) VARIABLE TRANSMITTANCE OPTICAL ELEMENT AND IMAGING OPTICAL SYSTEM INCLUDING THE SAME ARRANGED AT DISTAL END OF AN ENDOSCOPE

(75) Inventor: Shinya Matsumoto, Machida (JP)

(73) Assignee: Olympus Corporation, Tokyo (JP)

( * ) Notice: Subject to any disclaimer, the term of this patent is extended or adjusted under 35 U.S.C. 154(b) by 487 days.

(21) Appl. No.: 11/313,654

(22) Filed: Dec. 22, 2005

(65) Prior Publication Data
US 2006/0139780 A1 Jun. 29, 2006

(30) Foreign Application Priority Data
Dec. 24, 2004 (JP) ............................ 2004-373654

(51) Int. Cl.
*H01J 3/14* (2006.01)
*H01J 5/16* (2006.01)
(52) U.S. Cl. ................. 250/216; 356/450; 356/511; 356/512; 356/513
(58) Field of Classification Search ............... 250/216; 356/450, 511, 512, 513
See application file for complete search history.

(56) References Cited
U.S. PATENT DOCUMENTS
6,714,307 B2 * 3/2004 De Groot et al. ............ 356/512

FOREIGN PATENT DOCUMENTS
JP 2802061 7/1998

* cited by examiner

*Primary Examiner*—Seung C Sohn
(74) *Attorney, Agent, or Firm*—Arnold International; Bruce Y. Arnold

(57) ABSTRACT

A variable transmittance optical element is provided in an imaging optical system of an endoscope, and includes small etalons or multiple microscopic mirror that have an effective part that allows passage of a light beam received at a unit light receiving area that corresponds to an individual pixel, or a plurality of pixels, of an image pickup device that is provided in the imaging optical system of the endoscope. Each of said small etalons or microscopic mirrors have facing surfaces that are arranged so as to be parallel to one another on a transparent substrate; and the transparent substrate and an image pickup surface of the image pickup device are positioned so that each of the small etalons or microscopic mirrors allows passage of the light beam.

9 Claims, 19 Drawing Sheets

Fig. 18(b) After Coating
Fig. 18(a) Before Coating

Prior Art

Present Invention

VARIABLE TRANSMITTANCE OPTICAL ELEMENT AND IMAGING OPTICAL SYSTEM INCLUDING THE SAME ARRANGED AT DISTAL END OF AN ENDOSCOPE

CROSS REFERENCE TO RELATED APPLICATION

This application claims priority from JP 2004-373654 filed Dec. 24, 2004, the disclosure of which is hereby incorporated by reference.

BACKGROUND OF THE INVENTION

Japanese Patent Publication No. 2802061 discloses an endoscope with an observation optical system that contains a variable transmittance optical element known as an etalon wherein the etalon includes facing optical surfaces that are separated by an air gap spacing. The air gap spacing may be controlled by applying a voltage to a piezoelectric element so as to change the transmittance characteristics of the etalon.

FIG. 16 is an illustration showing the basic structure of such an etalon. The etalon shown in FIG. 16 comprises two substrates 35X-1 and 35X-2 having, on their facing surfaces, reflective coatings 35Y-1 and 35Y-2 with an air gap spacing d between the coatings on the facing surfaces. Of light entering from the substrate 35X-1, light of a very narrow range of wavelengths exits from reaches the substrate 35X-2 because of multiple beam interference that occurs between the reflective coatings 35Y-1 and 35Y-2.

As shown in FIG. 17, the peak transmittance wavelength of the etalon is shifted from Ta to Tb as the magnitude of the air gap spacing d is changed. A piezoelectric element can be used as a means to move the substrates to thereby change the magnitude of the air gap spacing d.

An etalon periodically exhibits peak transmittances for specific wavelengths of light as the air gap spacing d is changed. Generally, the spectral transmittance of an etalon is expressed by the following Equation (1):

$$T=1/\{1+[4R\sin^2(2\pi nd\cos\theta/\lambda)/(1-R)^2]\} \quad \text{Equation (1)}$$

where

T is the transmittance of the etalon for a given wavelength of light incident onto the etalon;

R is the reflectance of the reflective coatings;

n is the refractive index of the material, which generally is air—the refractive index of which is 1, between the substrates with attached coatings;

d is the air gap spacing between the substrates with attached coatings;

θ is the angle of incidence of the light onto the etalon, as measured from the surface normal; and λ is the wavelength of light incident onto the etalon.

The wavelengths for which an etalon has periodic peak spectral transmittances T occur where the following Equation (2) is satisfied:

$$m=2nd\cos\theta/\lambda\max \quad \text{Equation (2)}$$

where m is an integer, n, d, and θ are as defined above, and

λmax is one of the periodic wavelengths for which the etalon has a peak transmittance.

When light is incident onto an etalon at zero degrees (i.e., parallel to the surface normal), the etalon has peak spectral transmittances T for light of wavelengths (2/m) d. In this way, the wavelength of light that is transmitted through the etalon can be selected by changing the air gap spacing d. If an etalon is provided in the imaging optical system of an endoscope, observation images consisting of light having a desired wavelength can be obtained.

BRIEF SUMMARY OF THE INVENTION

The present invention relates to a variable transmittance optical element that is positioned in an imaging optical system of an endoscope and an endoscope imaging unit including the same. The present invention relates to a variable transmittance optical element that is formed of an array of small etalons, and to an endoscope imaging unit that is arranged at the distal end of an endoscope and includes such a variable transmittance optical element. The array of small etalons ensures that the facing substrate surfaces of each small etalon that support reflective films which form an air gap spacing are accurately parallel so as to produce a desired transmittance.

BRIEF DESCRIPTION OF THE DRAWINGS

The present invention will become more fully understood from the detailed description given below and the accompanying drawings, which are given by way of illustration only and thus are not limitative of the present invention, wherein:

FIG. 18(a) is a schematic diagram that shows a planar substrate;

FIG. 18(b) is a schematic diagram that shows the substrate of FIG. 18(a) after a coating has been applied that stresses the surface and causes it to deform so as to no longer be planar.

DETAILED DESCRIPTION

Figure 1A:
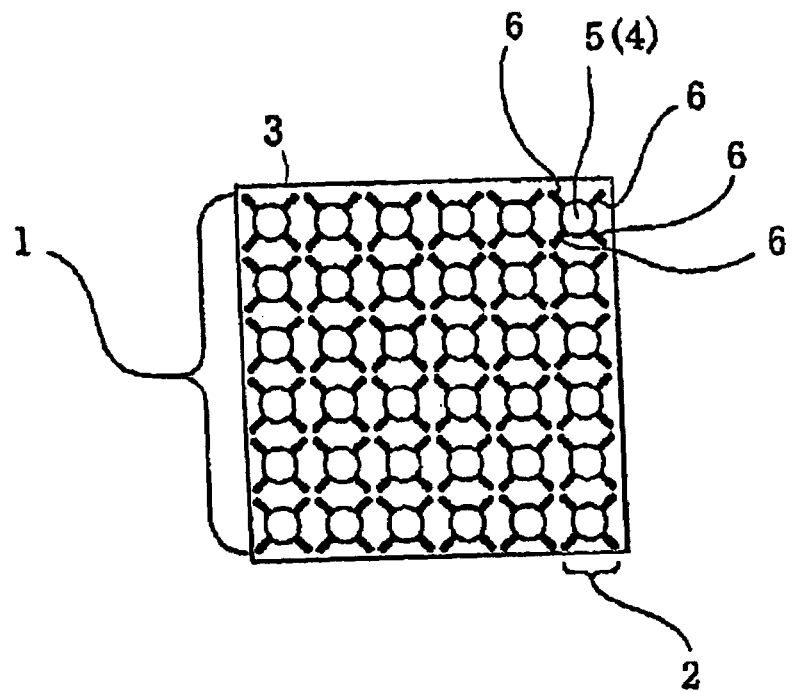
FIGS. 1(a) and 1(b) show the basic structure of a variable transmittance optical element according to the present invention, with FIG. 1(a) being a front view of the variable transmittance optical element, and FIG. 1(b) being a side view of the variable transmittance optical element.

In order for a variable transmittance optical element that is formed of an etalon to transmit a desired wavelength and achieve a high transmittance, it is essential that the facing surfaces of the etalon reflective coatings that cause optical interference be maintained parallel to each other and that the air gap spacing between these facing surfaces be controlled with high accuracy. This, in turn, generally requires that the facing surfaces of the etalon substrates, which support the facing surfaces of the etalon that cause optical interference, be planar to a high degree of accuracy. Generally, each facing surface of the substrate of an etalon must be planar within 1/50 to 1/100 of a wavelength, or better.

Optical thin films are deposited on each facing surface of an etalon substrate to form a reflective coating that causes optical interference. The optical thin films are made of one or more materials that are different from the substrate material. Therefore, the substrate receives stress from a deposited optical thin film. When a reflective coating is formed over a relatively large area of a substrate surface, and especially when the substrate thickness is small, the substrate may be subjected to large stresses and may be easily deflected, thereby hampering the substrate surface from being maintained as a planar surface with a high degree of accuracy.

The relationship between the length and thickness of a substrate versus substrate displacement when placed under stress by a coating will now be discussed.

FIGS. 18(a) and 18(b) are schematic diagrams that illustrate the length L, thickness b, and displacement $\epsilon$ of a substrate when the substrate is placed under stress due to there being a coating applied to the substrate surface, with FIG. 18(a) illustrating the substrate without a coating, and with FIG. 18(b) indicating the substrate with a coating that has deformed the substrate. The relationship between the displacement $\epsilon$ of a substrate due to being under stress from a coating versus other characteristics of the coating and substrate is set forth by Equation (3) below:

$$\epsilon = ((\beta(1-\gamma)E)/b^2) \int \rho(L,\mu)\mu(L)LdL \qquad \text{Equation (3)}$$

where $\beta$ is a coefficient, $\gamma$ is Poisson's ratio of the substrate material, E is Young's modulus of the substrate material, b is the thickness of the substrate, $\rho$ is the internal stress (here, a function of L and $\mu$), L is the substrate length, $\mu$ is the coating thickness (here, a function of L, and the integral extends over L, from L equal zero to L.

In Equation (3) above, the internal stress $\rho(L, \mu)$ when a uniform reflective coating is formed on the substrate is given by:

$$\rho(L,\mu) = \rho = \text{constant} \qquad \text{Equation (4).}$$

In such a case, the substrate displacement becomes:

$$\epsilon = ((\beta(1-\gamma)E\rho\mu)/b^2) \int LdL \qquad \text{Equation (5)}$$

with the integral extending over L, from L equals zero to L. Thus, $$\epsilon = ((\beta(1-\gamma)E\rho\mu)/\_b^2) \cdot L^2/2 \qquad \text{Equation (6)}$$

or, substituting $\alpha^2 = L^2/b^2$:

$$\epsilon = ((\beta(1-\gamma)E\rho\mu)/2) \cdot \alpha^2 \qquad \text{Equation (6')}$$

where $\alpha$ is the aspect ratio of the substrate contour, defined as equal to L/b.

When the substrate has a uniform reflective coating, as the aspect ratio becomes smaller, the substrate is subjected to a smaller displacement.

Figure 19B:
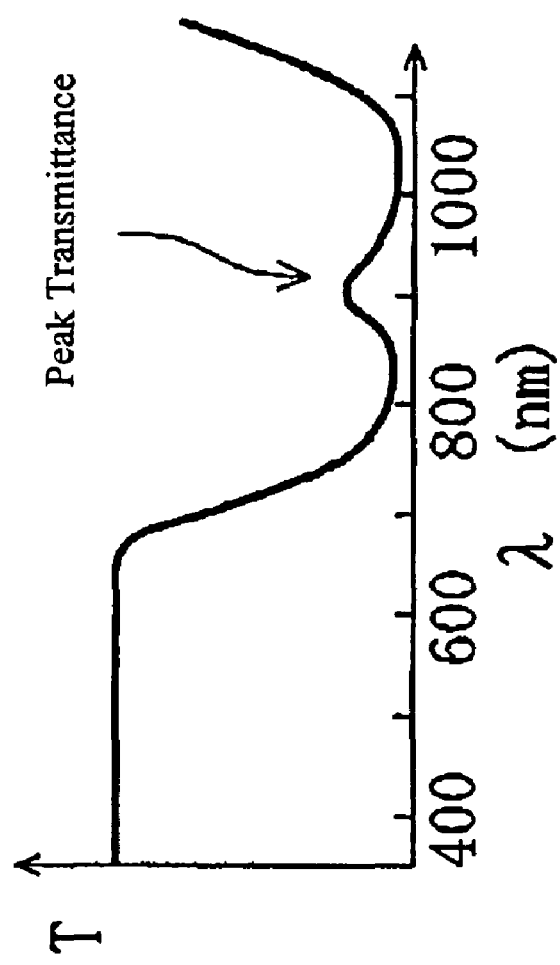
FIG. 19(b) shows the spectral transmittance of the etalon shown in FIG. 19(a)
Figure 19A:
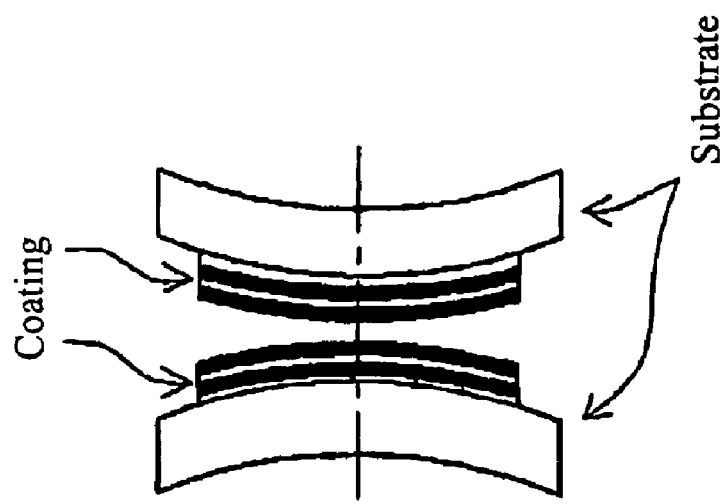
FIG. 19(a) shows an etalon with its substrates deformed due to stresses of the reflective coatings.

The etalon should be small for mounting in the imaging optical system of an endoscope. The substrate thickness is also required to be small (i.e., it is approximately 0.1 (mm). As a result, the substrate may be deformed under the stress of the reflective coating, making it difficult to maintain the substrate planar within a desired figure of tolerance. FIG. 19(a) is a schematic illustration showing an etalon with its substrates deformed under the stress of the reflective coatings and FIG. 19(b) shows the spectral transmittance of the etalon shown in FIG. 19(a). In this case, when a thin substrate has a reflective coating applied over a large area of the substrate, the substrate will be deflected as shown in FIG. 19(a), thereby preventing the substrate from maintaining a desired accuracy of being a planar surface. Consequently, as shown in FIG. 19(b), the spectral profile of the etalon will have a low peak transmittance and a large spectral width as measured between the half-maximum intensity points.

Figure 1B:
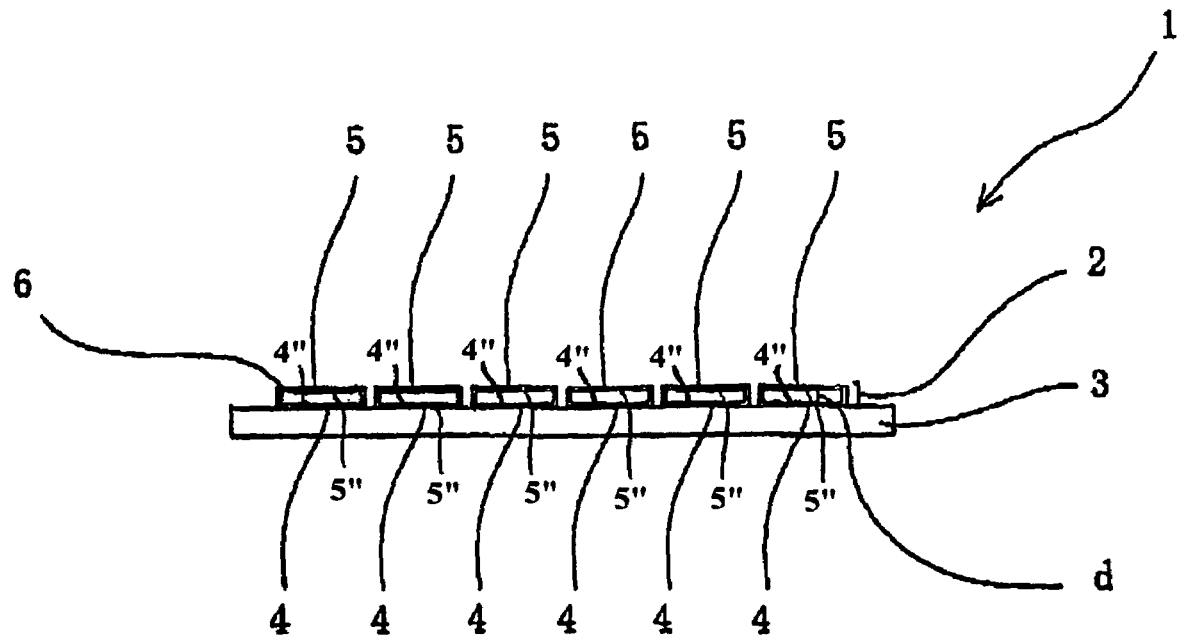

FIGS. 1(a) and 1(b) show the basic structure of a variable transmittance optical element 1 according to the present invention, with FIG. 1(a) being a front view, and with FIG. 1(b) being a side view. The variable transmittance optical element 1 of the present invention comprises small etalons 2 arranged in an array such that effective parts of the small etalons 2 allow passage of a light beam that is received at a unit light receiving area corresponding to an individual pixel, or several pixels, of an image pickup device. The image pickup device is provided in the imaging optical system of an endoscope, and the small etalons are arranged in a plane that faces the image pickup surface of the image pickup device. As shown in FIG. 1(b), substrates 4, 5 have reflective coatings 4", 5" on portions of their facing surfaces. Fixed by hinges 6, (see FIGS. 2(b) and 2(d)) the substrate 5 maintains an air gap spacing d relative to the substrate 4, where d is measured between the coated surfaces of the substrate. The small etalons 2 are arranged and fixed on a transparent substrate 3. A micro-actuator (not shown) is used to create an electrostatic force between the substrates 4, 5 so as to elastically deform the hinges 6, thereby changing the air gap spacing d.

The efficacy of the present invention will now be described hereinafter for a case in which each small etalon 2 corresponds to an individual pixel of the image pickup device.

Table 1 shows an image pickup device commonly used in endoscopes.

TABLE 1

| pixel size | number of pixels | effective part of the image pickup device |
| --- | --- | --- |
| 10 μm × 10 μm | 500 × 500 (250,000 pixels) | 5 mm × 5 mm |

Each pixel of the image pickup device has an aperture diameter of approximately 5 μm×5 μm.

When a prior art etalon is used with the image pickup device having the above structure, the substrate of the etalon is at least 5 mm×5 mm in size and 0.1 mm in thickness. Conversely, when a small etalon 2 is provided for an individual pixel, or a small number of pixels, as in the present invention, the substrate of the small etalon 2 is at least 5 (μm)×5 (μm) in size and 1 (μm) in thickness. Table 2 shows the aspect ratios of those two substrates.

TABLE 2

| | substrate size | coating size | length L | thickness d | aspect ratio |
| --- | --- | --- | --- | --- | --- |
| prior art | 5 mm × 5 mm | 5 mm × 5 mm | 5 mm | 0.1 mm | 50 |
| present invention | 5 μm × 5 μm | 5 μm × 5 μm | 5 μm | 1 μm | 5 |

As seen from Table 2, the aspect ratio can be significantly reduced by using an array of small etalons 2 in the variable transmittance optical element, as in the present invention. Consequently, the deformation of the substrate under the stress of the reflective coating can be reduced.

As described above, the variable transmittance optical element 1 of the present invention comprises multiple small etalons 2 having an effective part that allows passage of a light beam received at a unit light receiving area that corresponds to an individual pixel, or several pixels, of an image pickup device provided in the imaging optical system of an endoscope. The small etalons are arranged with their highly reflective facing surfaces parallel to one another and in a plane that faces the image pickup surface of the image pickup device. This ensures that the substrates have parallel facing surfaces, which in turn ensures that the highly reflective films are parallel to a high degree of accuracy so as to provide a desired transmittance.

The small etalons 2 have small substrates, which can be easily produced using a lithographic technique that is well known in the MEMS field. The small etalons 2 may be arranged on a cover glass surface that protects the image pickup surface of the image pickup device or on the surface of a lens or a filter that may be provided in the observation optical system. The air gap spacings of the small etalons 2 can be independently changed to obtain different spectral images in different areas of the image pickup surface of the image pickup device. Further, the peak transmittance wavelength shifts that occur when the light is incident onto small etalons 2 near the optical axis of the imaging optical system versus onto small etalons 2 that are positioned away from the optical axis of the imaging optical system can be corrected so as to obtain an image that is uniform in spectral content from the center of the image to the periphery thereof.

Figure 6A:
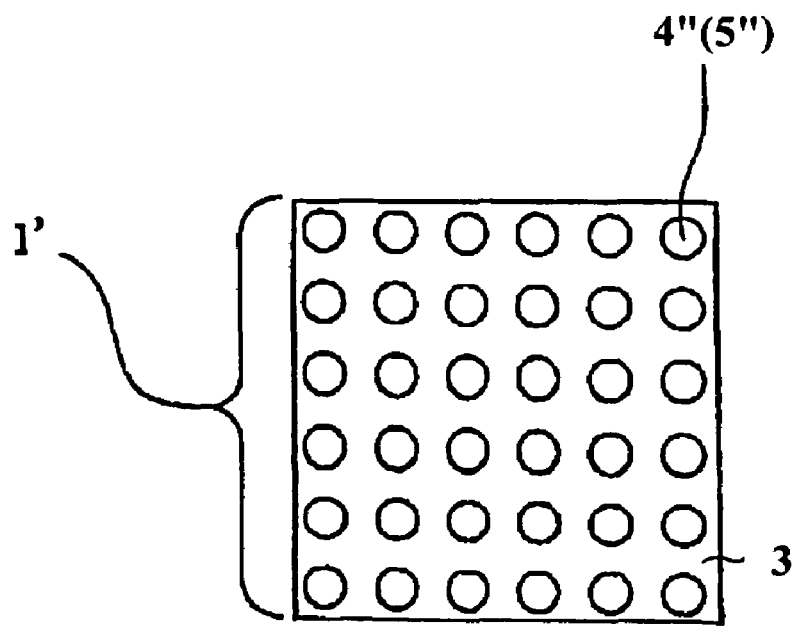
FIGS. 6(a) and 6(b) show an arrangement of small etalons in a variable transmittance optical element 1' according to Embodiment 2, with FIG. 6(a) being a front view and FIG. 6(b) being a side view.
Figure 6B:
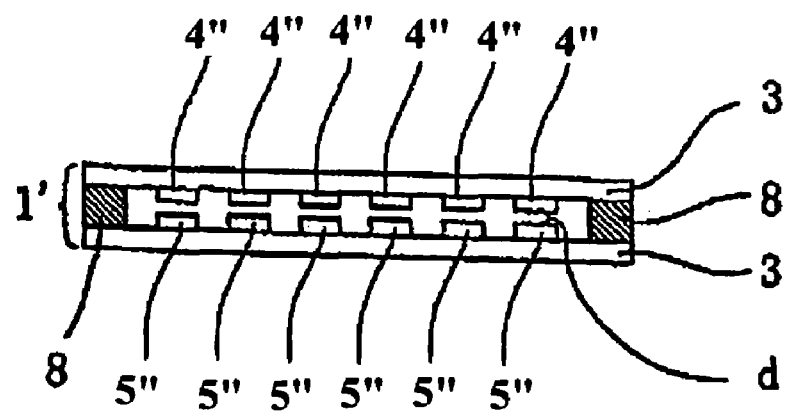

FIGS. 6(a) and 6(b) show another embodiment of the variable transmittance optical element of the present invention, with FIG. 6(a) being a front view and FIG. 6(b) being a side view. The variable transmittance optical element 1' of this embodiment includes reflective coatings 4" and 5" that are arranged in an array and have an effective part that allows passage of a light beam received at a unit light receiving area corresponding to an individual pixel, or several pixels, of an image pickup device that is provided in the imaging optical system of an endoscope. The reflective coatings 4" and 5" are parallel to a high degree of accuracy due to the facing surfaces of the substrates 3, 3 on which the reflective coatings are formed being planar surfaces to a high degree of accuracy. Piezoelectric elements 8, 8 are provided between the two substrates 3, 3 and serve to maintain an air gap spacing d between the reflective coatings 4" and 5". A drive circuit (not shown) for the variable transmittance optical element 1' is used to apply a voltage to the piezoelectric elements 8, 8 so as to deform the piezoelectric elements 8, 8. As a result, the air gap spacing d between the reflective coatings 4" and 5" may be changed. The etalon 1' is positioned so as to face the image pickup surface of the image pickup device.

Figure 20A:
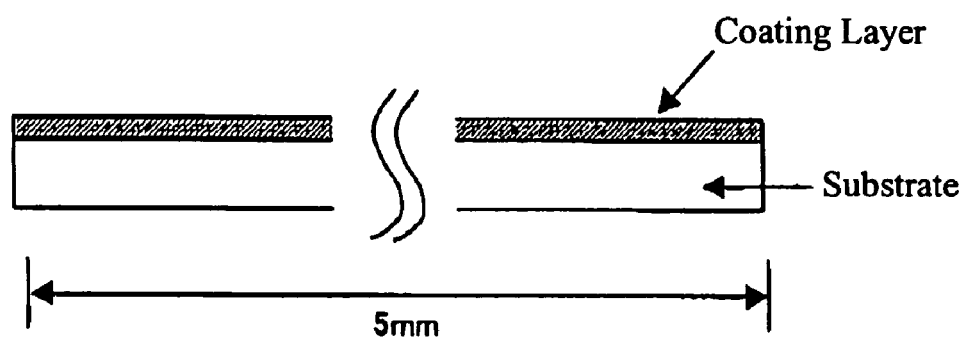
FIG. 20(a) shows a side view of a substrate and a single coating layer as in a prior art variable transmittance optical element.
Figure 20B:
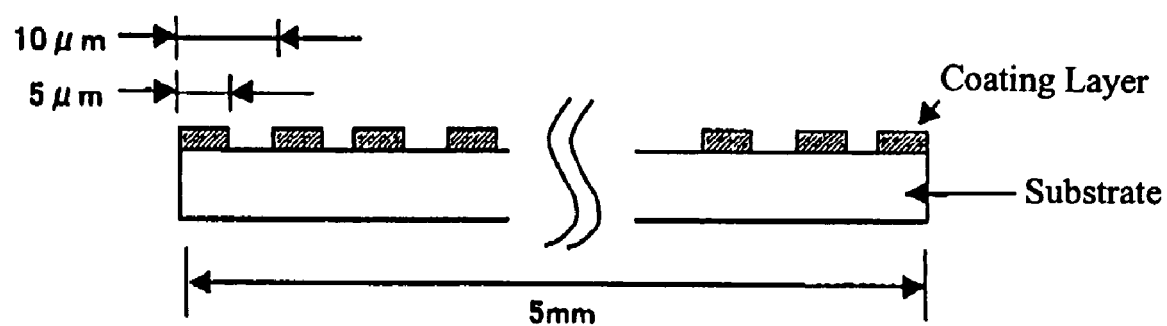
FIG. 20(b) shows a side view of a substrate and coating layer as in the variable transmittance optical element according to the present invention.

FIGS. 20(a) and 20(b) illustrate the structure of a portion of a variable transmittance optical element of this invention (as shown in FIG. 20(b)) in comparison with a portion of a variable transmittance optical element of the prior art (as shown in FIG. 20(a)). Both of the portions of the variable transmittance optical elements shown in FIGS. 20(a) and 20(b) have the same substrate dimensions. However, the reflective coatings on the substrate surface as shown in FIG. 20(b) have much smaller dimensions than the dimension of the single reflective coating that is applied to each substrate surface, of which FIG. 20(a) is representative. In FIG. 20(a) is illustrated a portion of a prior art variable transmittance optical element that is formed of a single etalon having a uniform reflective coating on the substrate surface. Conversely, the portion of the variable transmittance optical element shown in FIG. 20(b) has reflective coatings at intervals of a step function corresponding to the pixel pitch of the image pickup device. When the multiple reflective coatings of dimensions 5 (μm)×5 (μm) are formed at 5 μm intervals on a substrate of dimensions 5 (mm)×5 (mm), the displacement E due to the stress of the coating may be approximated by the following calculation:

$$\epsilon = ((\beta(1-\gamma)E\rho\mu/b^2)\Sigma(\int LdL + \int LdL) \quad \text{Equation (7)}$$

where the summation Σ extends from n=1 to n=500, the first integral within the parenthesis on the right side of Equation (7) is with respect to L, with L extending from L=0.005 (n−1) to L=0.005 (2n−1), and the second integral within the parenthesis on the right side of Equation (7) is with respect to L, with L extending from L=0.005 (2n−1) to L=0.01 n.

The first term in the parenthesis on the right side of Equation (7) determines the area of the reflective coatings on the substrate surface, and the second term in the parenthesis on the right side of Equation (7) determines the remaining area where no reflective coatings are provided on the substrate surface. Therefore, the second term may be deleted and the Equation (7) may be rewritten as follows:

$$\epsilon = ((\beta(1-\gamma)E\rho\mu)/b^2)\Sigma(\int LdL) \quad \text{Equation (7')}$$

where the summation Σ extends from n=1 to n=500, and the integral within the parenthesis on the right side of Equation (7') is with respect to L, with L extending from L=0.005 (n−1) to L=0.005 (2n−1).

When a single, uniform reflective coating of dimensions 5 (mm)×5 (mm) shown in FIG. 20(a) is formed on a substrate of dimensions 5 (mm)×5 (mm), the displacement ϵ due to the stress of the coating may be approximated by the following calculation:

$$\epsilon = ((\beta(1-\gamma)E\rho\mu)/b^2)\int LdL \quad \text{Equation (8)}$$

with the integral extending over L, from L equals zero to 5.

As is readily apparent from the Equations (7') and (8), the displacement ϵ depends on the area of the reflective coating on the substrate when the thickness of the substrate is kept constant. Therefore, a comparison of Equation (7') and Equation (8) reveals that the variable transmittance optical element 1', by having multiple small etalons instead of one large etalon, is subject to much smaller errors due to displacement of the substrate(s) than is variable transmittance optical element of the prior art. In the above calculation, it has been assumed that the substrate has a length L of 5 mm. However, the design of the variable transmittance optical element 1' enables the substrate to undergo much less displacement due to stress of the coating than in the prior art variable transmittance optical element, regardless of the value of L.

As described above, a variable transmittance optical element that is formed with reflective coatings 4" and 5" that have an effective part that allows passage of a light beam received at a unit light receiving area corresponding to an individual pixel, or several pixels, of an image pickup device that is positioned in the imaging optical system of an endoscope has improved transmittance characteristics as compared with a single etalon, variable transmittance optical element of the prior art.

Several embodiments of the present invention will now be described with reference to the drawings.

Embodiment 1

Figure 2A:
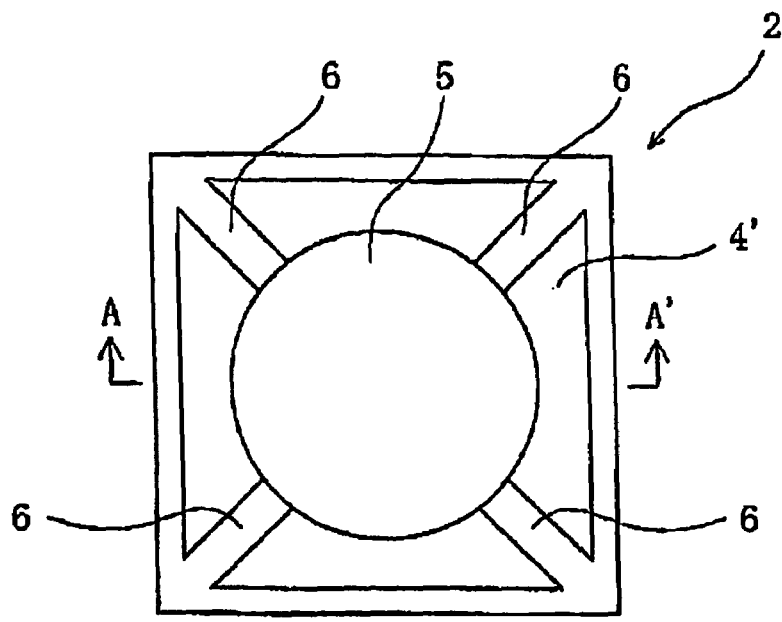
FIGS. 2(a)-2(d) show the basic structure of a variable transmittance optical element according to Embodiment 1, with FIG. 2(a) being a front view of a single small etalon, FIG. 2(b) being a side view of a single small etalon in a first transmittance state, with FIG. 2(c) being a side view of one arrangement of small etalons that are included in the variable transmittance optical element according to a first embodiment, and FIG. 2(d) being a side view of the single small etalon when in a second transmittance state.
Figure 2B:
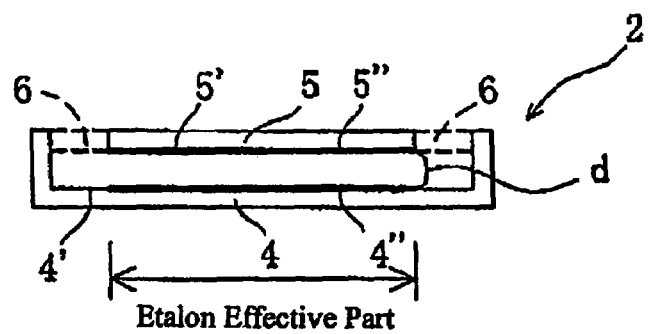
Figure 2C:
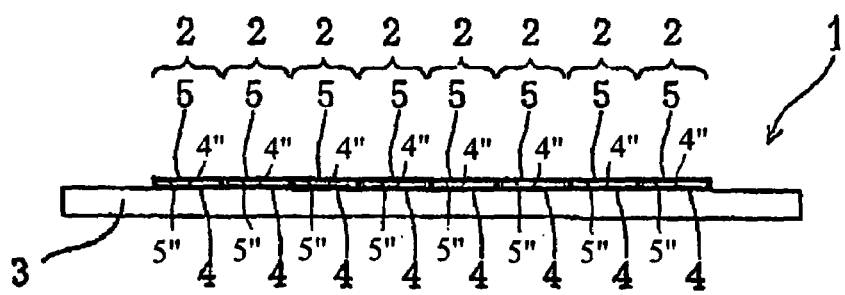
Figure 2D:
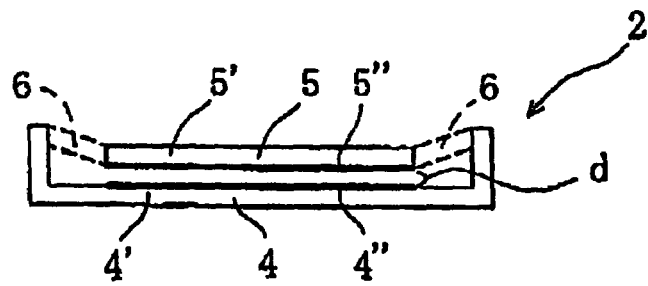

FIGS. 2(a)-2(d) show the structure of a variable transmittance optical element 1 according to Embodiment 1, with FIG. 2(a) being a front view of a small etalon 2, with FIG. 2(b) being a cross-sectional view taken along the line A-A' in FIG. 2(a), with FIG. 2(c) being a partial side view of the small etalons 2 that are arranged on a transparent substrate 3, and with FIG. 2(d) being an illustration to explain the movement of the small etalons 2 when the air gap spacing is changed.

The variable transmittance optical element of the present embodiment comprises small etalons 2 having an effective part that allows passage of a light beam that is received at a unit light receiving area corresponding to an individual pixel, or several pixels, of an image pickup device. The variable transmittance optical element is provided in the imaging optical system of an endoscope, and the small etalons are arranged so that their reflective surfaces are parallel on a transparent substrate 3. As shown in FIGS. 2(b) and 2(d), small etalon substrates 4 and 5 of each small etalon 2 have reflective coatings 4" and 5" on their respective facing surfaces 4' and 5'. Fixed by hinges 6, the small etalon substrate 5 maintains an air gap spacing relative to the small etalon substrate 4 so that the spacing between the reflective coatings 4" and 5" is d. In a small etalon 2, a voltage is applied to electrodes (not shown) on the small etalon substrates 4 and 5 so as to create an electrostatic force between the small etalon substrates 4 and 5. This electrostatic force then causes the small etalon substrate 5 to move relative to the small etalon substrate 4. A part of the hinge 6 and the small etalon substrate 4 where no reflective coating is provided has a light-shielding means (not shown) such as a light-shielding coating or a light-shielding frame.

Figure 3A:
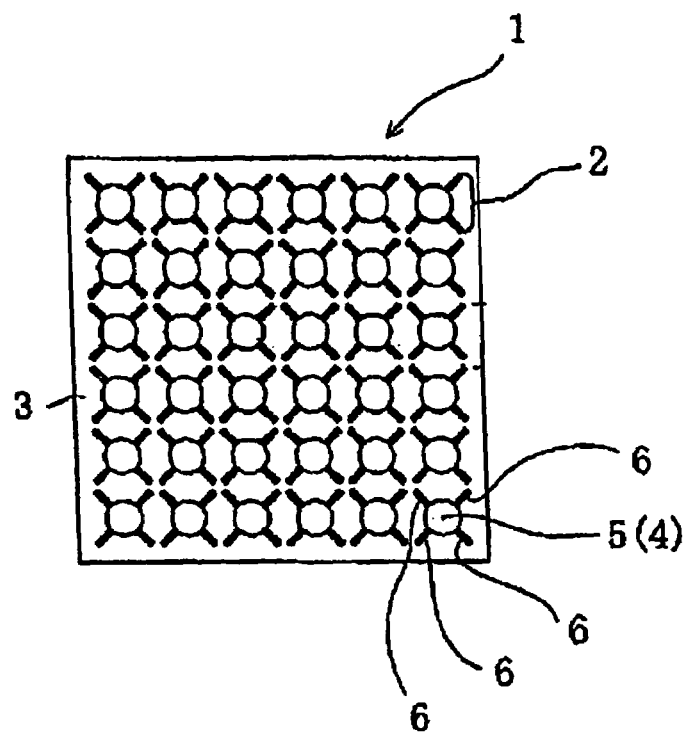
FIGS. 3(a) and 3(b) show an arrangement of small etalons 2 in a variable transmittance optical element 1 according to Embodiment 1 of the present invention, with FIG. 3(a) being a front view, and FIG. 3(b) being a side view.
Figure 3B:
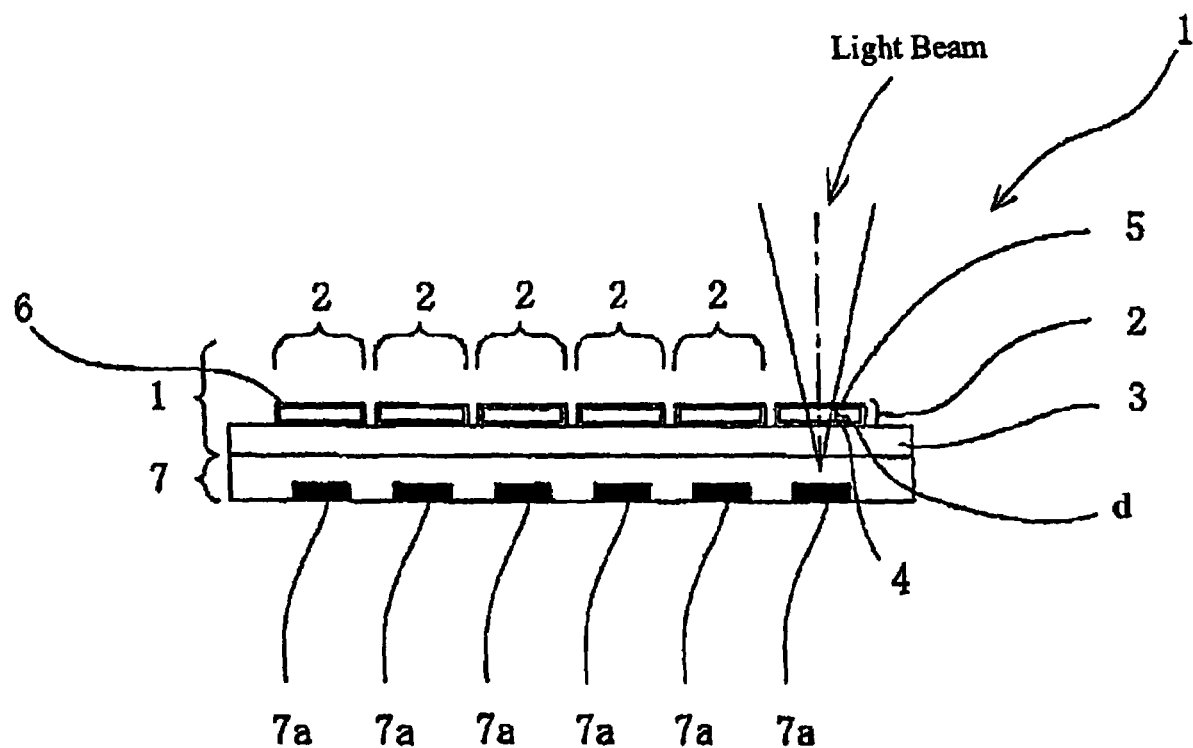

FIGS. 3(a) and 3(b) show an arrangement of the small etalons 2, with FIG. 3(a) being a front view of the variable transmittance optical element 1, and FIG. 3(b) showing the positional relationship between the variable transmittance optical element 1 and the image pickup surface 7 of the image pickup device. In this case, the variable transmittance optical element 1 is placed immediately before the image pickup surface 7 of the image pickup device in an endoscope. The small etalons 2 that are arranged in parallel on the transparent substrate 3 have an effective part that allows passage of a light beam entering a single pixel 7a. The transparent substrate 3 and the image pickup surface 7 of the image pickup device are positioned so that each small etalon 2 allows the passage of a light beam entering an individual pixel 7a.

Figure 4A:
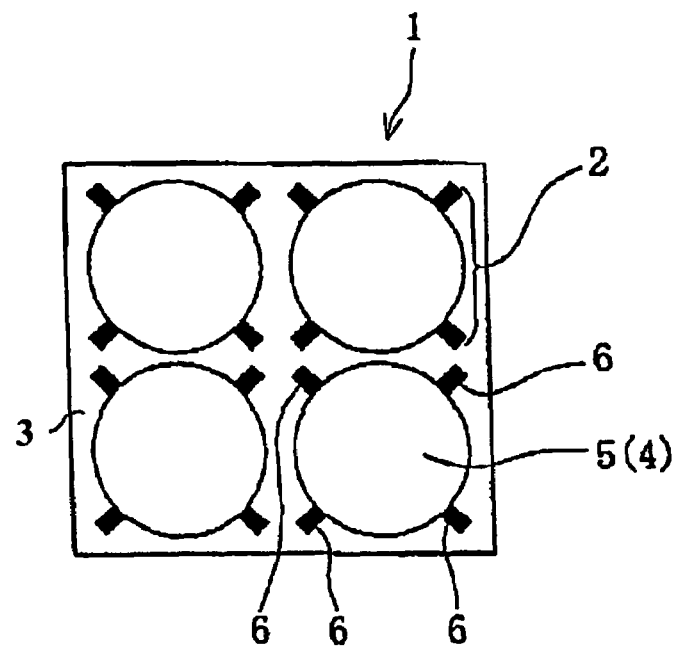
FIGS. 4(a) and 4(b) show another possible arrangement of small etalons 2 in the variable transmittance optical element 1 according to Embodiment 1 of the invention, with FIG. 4(a) being a front view, and FIG. 4(b) being a side view.
Figure 4B:
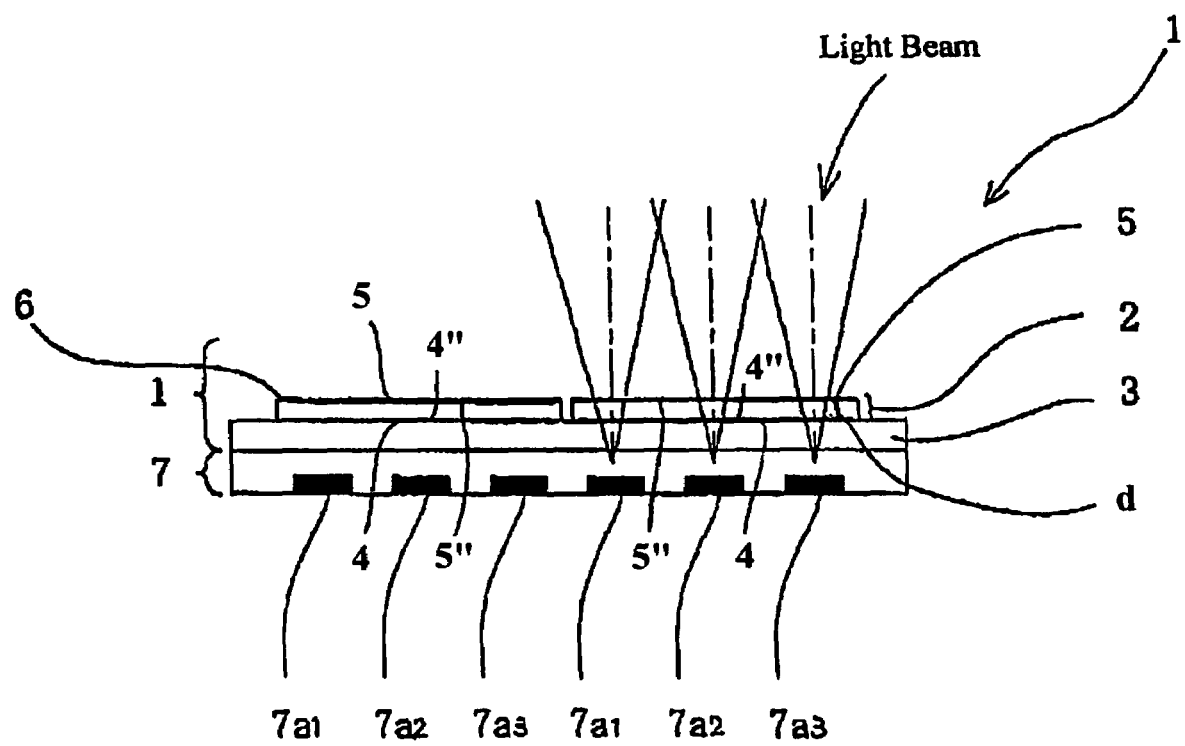

FIGS. 4(a) and 4(b) show another arrangement of the small etalons 2, with FIG. 4(a) being a front view of the variable transmittance optical element 1, and FIG. 4(b) showing the positional relationship between the variable transmittance optical element 1 and the image pickup surface 7 of the image pickup device. In this case, the variable transmittance optical element 1 is placed immediately before the image pickup surface 7 of the image pickup device in an endoscope. The small etalons 2 that are arranged in parallel on the transparent substrate 3 have an effective part that allows passage of a light beam entering multiple pixels 7a (for example, pixels 7a1, 7a2, and 7a3 in FIG. 4(b)). The transparent substrate 3 and the image pickup surface 7 of the image pickup device are positioned so that each small etalon 2 allows passage of a light beam entering multiple pixels 7a (for example, pixels 7a1, 7a2, and 7a3 in FIG. 4(b)).

Figure 5A:
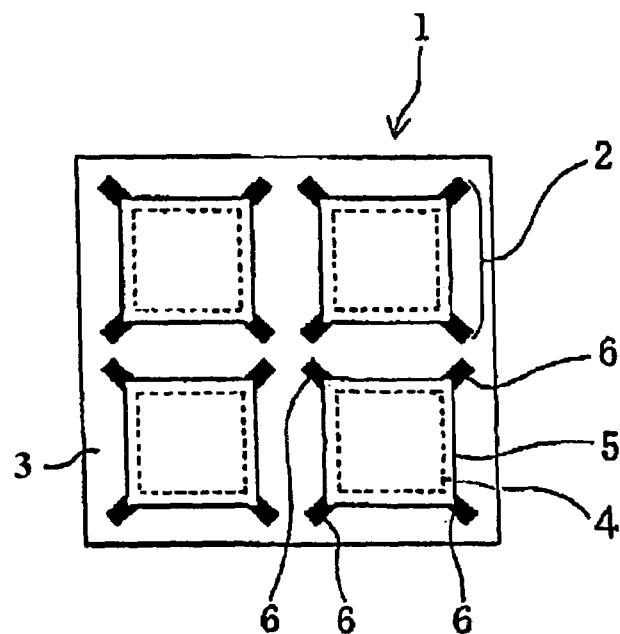
FIGS. 5(a) and 5(b) show still another arrangement of small etalons 2 in the variable transmittance optical element 1 according to Embodiment 1 of the invention, with FIG. 5(a) being a front view, and FIG. 5(b) being a side view.
Figure 5B:
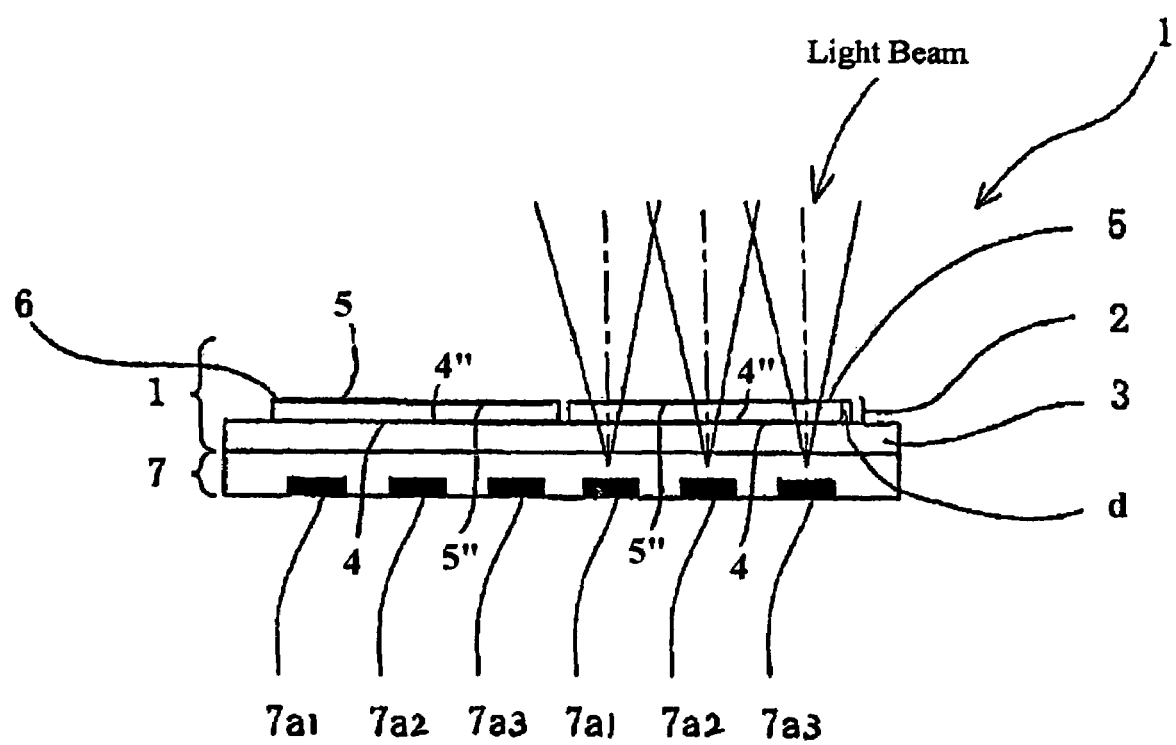

FIGS. 5(a) and 5(b) show yet another arrangement of the small etalons 2, with FIG. 5(a) being a front view of the variable transmittance optical element 1, and FIG. 5(b) showing the positional relationship between the variable transmittance optical element 1 and the image pickup surface 7 of the image pickup device. In this case, the variable transmittance optical element 1 is placed immediately before the image pickup surface 7 of the image pickup device provided in an endoscope. The small etalons 2 that are arranged in parallel on the transparent substrate 3 have an effective part that allows passage of a light beam entering multiple pixels 7a (for example, pixels 7a1, 7a2, and 7a3 in FIG. 5(b)). The transparent substrate 3 and the image pickup surface 7 of the image pickup device are positioned so that each small etalon 2 allows passage of a light beam entering multiple pixels (for example, pixels 7a1, 7a2, and 7a3 in FIG. 5(b)). Further, the small etalon substrate 5 away from the image pickup surface 7 of the image pickup device has a larger effective part than the small etalon substrate 4 that is closer to the image pickup surface 7 of the image pickup device. Thus, the small etalon substrate 5 does not cut into a light beam entering the pixel 7a when moved relative to the small etalon substrate 4, preventing an image from being partially missing or darkening. Additionally, the small etalon substrates 4 and 5 are not necessarily circular, as shown in FIG. 5(a).

As described above, the variable transmittance optical element 1 includes the small etalons 2 having an effective part that allows passage of a light beam received at a unit light receiving area corresponding to an individual pixel, or several pixels, of an image pickup device. The variable transmittance optical element is provided in the imaging optical system of an endoscope and the small etalons are arranged in parallel on a plane so as to face the image pickup surface of the image pickup device. This ensures that substrates having planar surfaces are provided, with the planar surfaces being more accurate than could be obtained with prior art variable transmittance optical elements. Hence, when provided in the imaging optical system of an endoscope, the variable transmittance optical element according to the invention enables improved spectral accuracy, and allows bright endoscope images of desired wavelength components to be obtained. In the variable transmittance optical element 1 shown in FIGS. 3(a) and 3(b), the air gap spacing d of the individual small etalons 2 can be independently controlled to form a color mosaic filter having different spectral transmittances for different pixels.

Embodiment 2

Figure 7A:
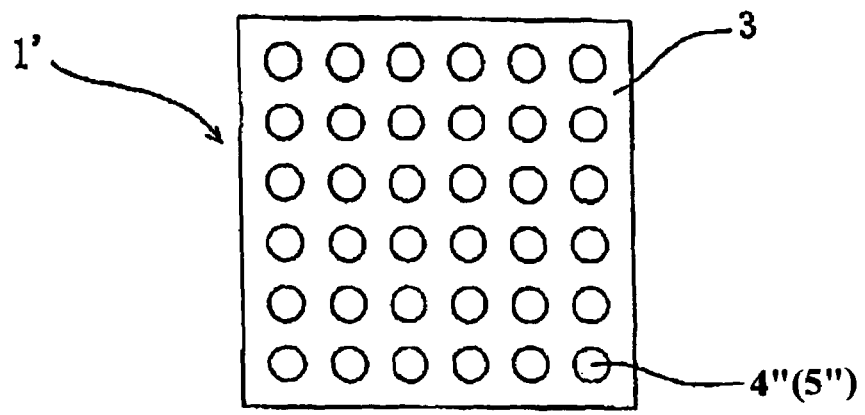
FIGS. 7(a) and 7(b) show the structure of the variable transmittance optical element 1' according to Embodiment 2 of the present invention, with FIG. 7(a) being a front view and FIG. 7(b) being a side view.
Figure 7B:
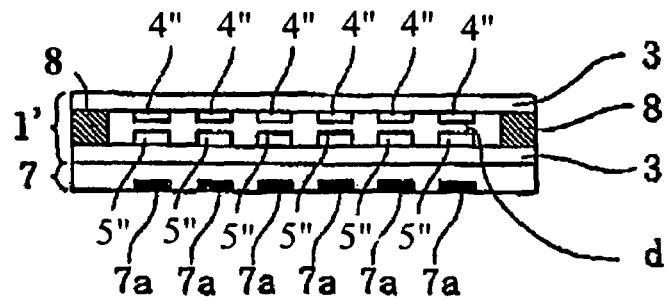

FIGS. 7(a) and 7(b) show a structure of a variable transmittance optical element 1' according to Embodiment 2 of the present invention, with FIG. 7(a) being a front view of the variable transmittance optical element 1', and FIG. 7(b) showing the positional relationship between the variable transmittance optical element 1' and the image pickup surface 7 of the image pickup device. The variable transmittance optical element 1' of this embodiment is placed immediately before the image pickup surface 7 of the image pickup device provided in an endoscope. The variable transmittance optical element 1' includes multiple microscopic mirrors 4" and 5" that have an effective part that allows passage of a light beam received at a unit light receiving area corresponding to an individual pixel of the image pickup device. Pairs of the multiple microscopic mirrors 4", 5" are arranged in parallel on the facing surfaces of transparent substrates 3, 3. The microscopic mirrors 4", 5" are produced by depositing reflective coatings on each substrate. A voltage is applied to a piezoelectric element 8 that is positioned between the transparent substrates 3, 3. Consequently, at least one of the substrates 3, 3 may be moved so as to change the mutual distance d between the facing microscopic mirrors 4", 5" with attached reflective coatings. The facing surfaces of the transparent substrates 3, 3 have a sufficient level of planarity before the microscopic mirrors 4" and 5" are formed thereon. The transparent substrate 3 and the image pickup surface 7 of the image pickup device are positioned so that the microscopic mirrors 4", 5" allow passage of a light beam entering an individual pixel 7a.

Figure 8A:
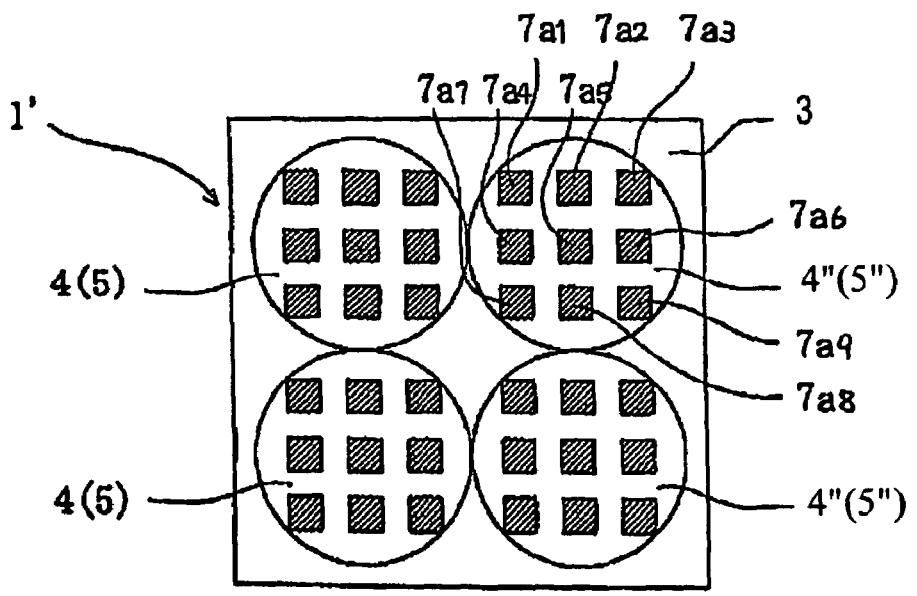
FIGS. 8(a) and 8(b) show another structure of the variable transmittance optical element 1' according to Embodiment 2 of the present invention, with FIG. 8(a) being a front view and FIG. 8(b) being a side view.
Figure 8B:
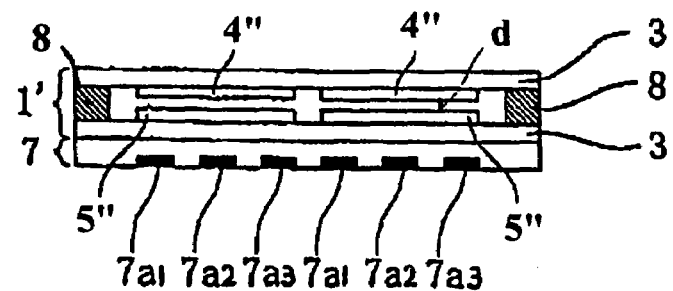

FIGS. 8(a) and 8(b) show another structure of the variable transmittance optical element 1' of the present embodiment, with FIG. 8(a) being a front view of the variable transmittance optical element 1', and FIG. 8(b) showing the positional relationship between the variable transmittance optical element 1' and the image pickup surface 7 of the image pickup device.

In the case shown in FIGS. 8(a) and 8(b), the variable transmittance optical element 1' is placed immediately before the image pickup surface 7 of the image pickup device in an endoscope. The variable transmittance optical element 1' includes multiple microscopic mirrors 4", 5" that have an effective part that allows passage of a light beam received at a unit light receiving area corresponding to multiple pixels (7a1 to 7a9 in FIG. 8(a)) of the image pickup device and are arranged in parallel on the facing surfaces of transparent substrates 3, 3. The microscopic mirrors 4", 5" are produced by depositing reflective coatings on a substrate. A voltage is applied to a piezoelectric element 8, such as one that is provided between the transparent substrates 3, 3 so as to deform the piezoelectric element 8. Thus, at least one of the substrates 3, 3 moves to change the mutual distance d between the facing surfaces of the microscopic mirrors 4", 5". The facing surfaces of the transparent substrates 3, 3 have a sufficient accuracy of planarity before the microscopic mirrors 4", 5" are formed on these facing surfaces.

The transparent substrate 3 and the image pickup surface 7 of the image pickup device are positioned so that the microscopic mirrors 4", 5" allow passage of a light beam entering multiple pixels (i.e., pixels 7a1 to 7a9 in FIG. 8(a)). The portions of the substrate 3 where no microscopic mirrors 4", 5" are provided have a light-shielding means (not illustrated), such as a light-shielding mask.

As described above, the variable transmittance optical element of this embodiment includes microscopic mirrors 4" and 5" that have an effective part that allows passage of a light beam that is received at a unit light receiving area corresponding to an individual pixel, or multiple pixels, of an image pickup device. The variable transmittance optical element is provided in the imaging optical system of an endoscope and microscopic mirrors are arranged in parallel on the facing surfaces of two transparent substrates 3, 3. Such a structure ensures that the two transparent substrates have planar surfaces that are more accurately planar than available with prior art variable transmittance optical elements. Hence, the variable transmittance optical element that is provided in the imaging optical system of an endoscope according to the present invention has improved spectral accuracy, and endoscope observation images having desired wavelength components can be obtained.

The microscopic mirrors 4" and 5" having a desired area can be formed on a substrate surface by: (a) masking the substrate surface and then depositing a reflective coating on the masked substrate surface or (b) by depositing a reflective coating on the substrate surface and then etching the reflective coating.

Embodiment 3

Figure 9A:
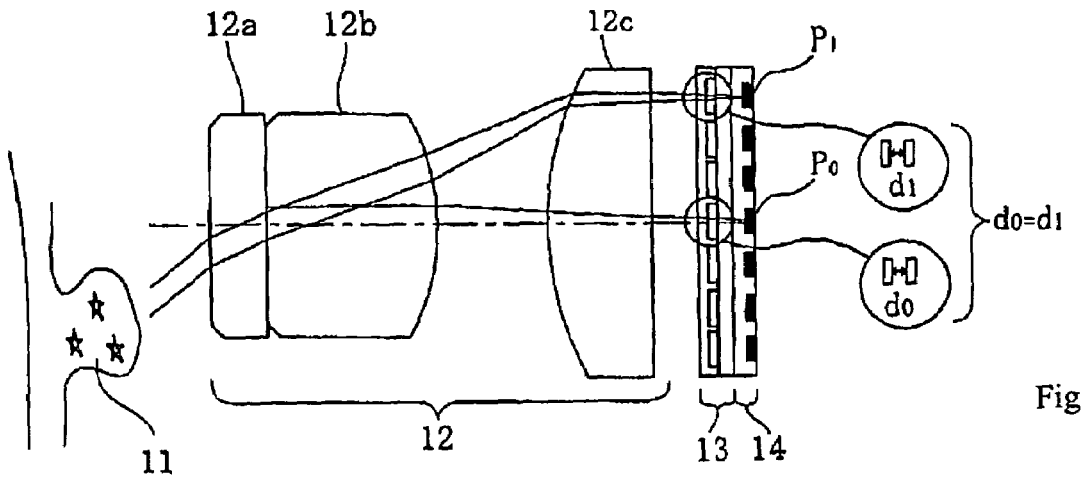
FIGS. 9(a)-9(c) show a structure of an endoscope imaging unit according to Embodiment 3 of the present invention.
Figure 9B:
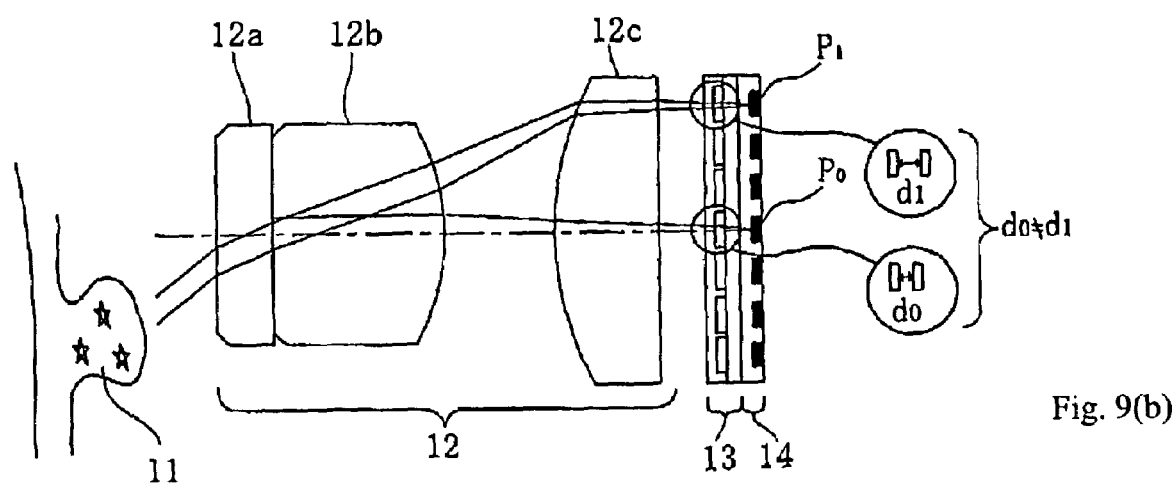
Figure 9C:
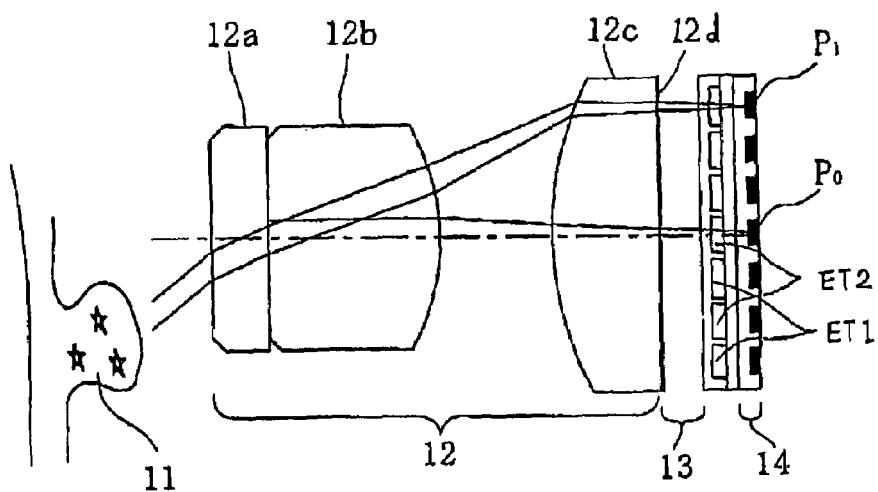

FIGS. 9(a)-9(c) show a structure of an endoscope imaging unit according to Embodiment 3 of the present invention. Each of these figures shows a subject 11 (i.e., a portion of a living body), an objective lens 12, a variable transmittance optical element 13, and an image pickup surface 14 of an image pickup device, such as a CCD. The objective lens 12 (formed of the lens elements 12a, 12b, and 12c) is a nearly telecentric optical system. Therefore, light enters the image pickup surface 14 of the image pickup device at nearly the same angle throughout the image pickup area. The variable transmittance optical element 13 is formed of multiple small etalons arranged in a planar array facing the image pickup surface 14 of the image pickup device as in Embodiment 1.

In each of FIGS. 9(*a*)-9(*c*), $P_0$ is an imaging point on the optical axis. Although not illustrated, d0 is the air gap spacing of a small etalon through which a light beam enters the point $P_0$. $P_1$ is the maximum image height point on the image pickup surface 14 of the image pickup device and (although not illustrated) d1 is the air gap spacing of a small etalon through which a light beam enters the point $P_1$.

In the endoscope imaging unit of the present embodiment, light enters the image pickup surface 14 of the image pickup device at nearly the same angle throughout the image pickup area. Thus, by merely equally changing the air gap spacing of the small etalons from the imaging point on the optical axis $P_0$ to the maximum image height point $P_1$ (with d0 equal to d1), light of the same wavelength component is separated throughout the image pickup area to obtain a spectral image of the subject 11.

Alternatively, as shown in FIG. 9(*b*), by using the small etalons having different air gap spacings between the imaging point on the optical axis $P_0$ and the maximum image height point $P_1$ (with d0 not equal to d1), different spectral data of the subject 11 can be obtained for different image pickup positions. In this way, multiple spectral data can be obtained for diagnosis of parts requiring close-examination.

FIG. 9(*c*) is an illustration showing a structure of an endoscope imaging unit for obtaining fluorescent images of the subject 11. The endoscope imaging unit of the present embodiment comprises small etalons ET1 and ET2 having different transmittances in every other row (line) of pixels. An image processor (not shown) is used to separately obtain an image captured by the rows of pixels with the small etalon ET1 and an image captured by the rows of pixels with the small etalon ET2. A lens 12*c*, which is nearest the image pickup device, has on the image pickup device side a flat surface on which a coating 12*d* that cuts off light unnecessary for forming images is provided.

FIGS. 10(*a*) and 10(*b*) show the transmittances of the small etalons ET1 and ET2, respectively. As shown in FIG. 10(*a*), the small etalons ET1 have a variable peak transmittance wavelength in the wavelength range of 400 nm-600 nm. On the other hand, the small etalons ET2 have a variable peak transmittance wavelength in the wavelength range of 600 nm-800 nm, as shown in FIG. 10(*b*). For example, an illumination unit (not illustrated) may be used to illuminate living tissue with two different excitation light beams, separately obtaining an auto-fluorescent image of fluorescent substances that occur naturally in the living tissue and a fluorescent image from a fluorescent probe that has been introduced into the living tissue. It is known that living tissue mainly absorbs light of wavelengths 500 nm or shorter and emits auto-fluorescence in the blue to green wavelength range. Auto-fluorescent images of living tissue can be obtained by illuminating the living tissue with light of wavelengths 500 nm or shorter and capturing images using rows of pixels covered with the small etalon ET1. On the other hand, a fluorescent probe using a dye that absorbs light of wavelengths 500 nm or longer and emits fluorescence in the near infrared range is known, by which fluorescent images from a fluorescent probe that has previously been introduced into living tissue can be obtained by illuminating the living tissue with light of wavelengths 500 nm or longer, and capturing images using the rows of pixels covered with the small etalons ET2.

The air gap spacings of the small etalons ET1 can be changed to select any wavelengths of light in the range of 400 nm-600 nm for obtaining fluorescent images. Further, the air gap spacings of the small etalons ET2 can be changed to select any wavelengths of light in the range of 600 nm-800 nm for obtaining fluorescent images.

Light that is used for exciting auto-fluorescent substances such as collagen and porphyrin in living tissue and light that is used for exciting fluorescent probes must be eliminated before reaching the image pickup surface 14 of the image pickup device. For example, when 400 nm to 430 nm wavelength light is used to excite auto-fluorescent substances in living tissue, and when 650 nm to 670 nm wavelength light is used to excite fluorescent probes that have previously been introduced into living tissue, an excitation light cut-off filter is used, such as the coating 12*d*, that cuts off these excitation lights so that they do not reduce contrast in the images.

Figure 11:
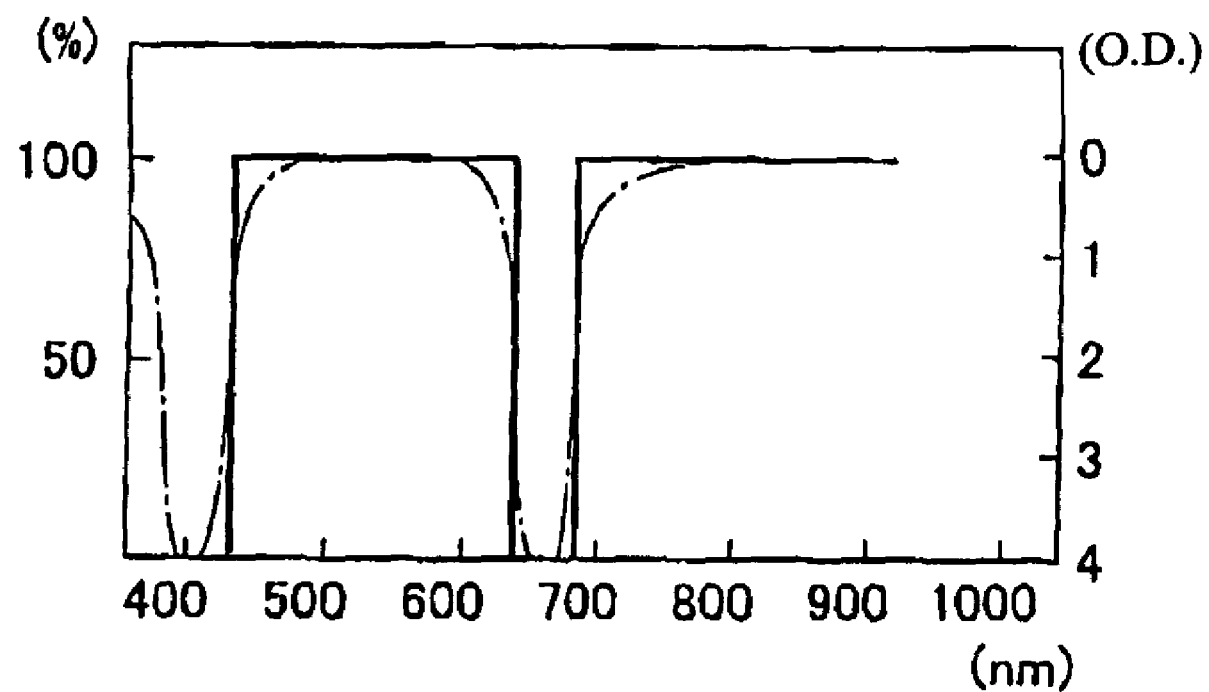
FIG. 11 shows the optical transmission properties of a coating 12d of Embodiment 3 that cuts off undesired light that is unnecessary for forming images.

Referring to FIG. 11, the solid line indicates the ideal % transmittance property of the excitation light cut-off filter 12*d* for light rays incident on the filter surface at an angle of 0°, for which the left-side vertical scale applies. On the other hand, the chain line indicates the best optical density property of the excitation light cut-off filter 12*d* for light rays incident on the filter surface at an angle of 0°, which may be realized as an actual filter. The right-side vertical scale applies to the optical density property. That is, the ideal state is shown by the % transmittance. The actual state is shown by the optical density. Optical density is defined as set forth in Equation (9) below:

$$O.D.=\log_{10}(I/I') \qquad \text{Equation (9)}$$

where

I is the intensity of light that is incident on the filter, and

I' is the intensity of light that is transmitted through the filter.

According to FIG. 1, the excitation light cut-off filter has an average transmittance of 70% or higher in a range between 440 nm and 640 nm and in a range between 690 nm and 790 nm and an optical density of 4 or greater in a range between 400 nm and 430 nm and in a range between 650 nm and 670 nm. Thus, the excitation light cut-off filter cuts off the two excitation light beams before they reach small etalons ET1 and ET2. With the above structure, multiple fluorescent lights from living tissue simultaneously illuminated with two different excitation light beams can be separated by the small etalons ET1 and ET2 before forming images.

Embodiment 4

Figure 12A:
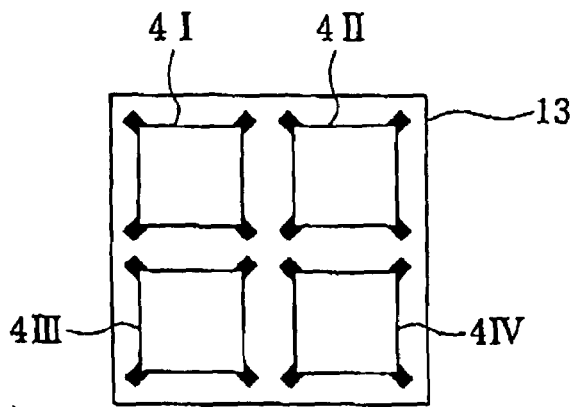
FIGS. 12(a)-12(c) show the structure of an endoscope imaging unit according to Embodiment 4 of the present invention, with FIG. 12(a) being a front view of a variable transmittance optical element, with FIG. 12(b) illustrating a view field 0 of the objective optical system 12 relative to a subject 11, and with FIG. 12(c) showing an exemplary display of images that may be captured by the endoscope imaging unit according to Embodiment 4.
Figure 12B:
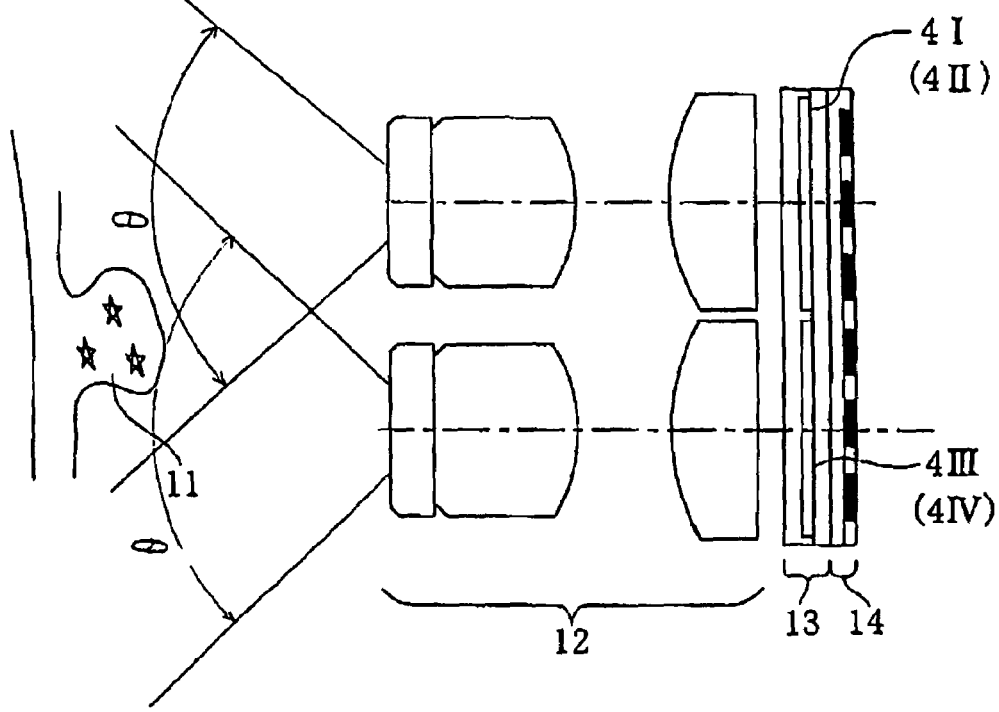

FIGS. 12(*a*)-12(*c*) show the structure of an endoscope imaging unit according to Embodiment 4 of the present invention, with FIG. 12(*a*) showing the structure of a variable transmittance optical element 13 installed in the endoscope imaging unit, with FIG. 12(*b*) illustrating a field of view θ of the objective optical system 12 relative to a subject 11, and with FIG. 12(*c*) showing an exemplary display of images that may be captured by the endoscope imaging unit according to this embodiment. As shown in FIGS. 12(*a*) and 12(*b*), the image pickup surface 14 of the image pickup device is divided into four image pickup areas where images of the subject 11 are formed by four corresponding objective optical systems 12.

The variable transmittance optical element 13 includes four small etalons 4I, 4II, 4III, and 4IV arranged in parallel on a transparent substrate facing the image pickup surface 14 of the image pickup device. The small etalons 4I, 4II, 4III, and 4IV have an effective part that allows passage of a light beam entering each of the image pickup areas. The variable transmittance optical element 13 and the image pickup surface 14 of the image pickup device are positioned so that the small etalons 4I, 4II, 4III, and 4IV allow passage of light beams entering the respective image pickup areas.

Figure 10A:
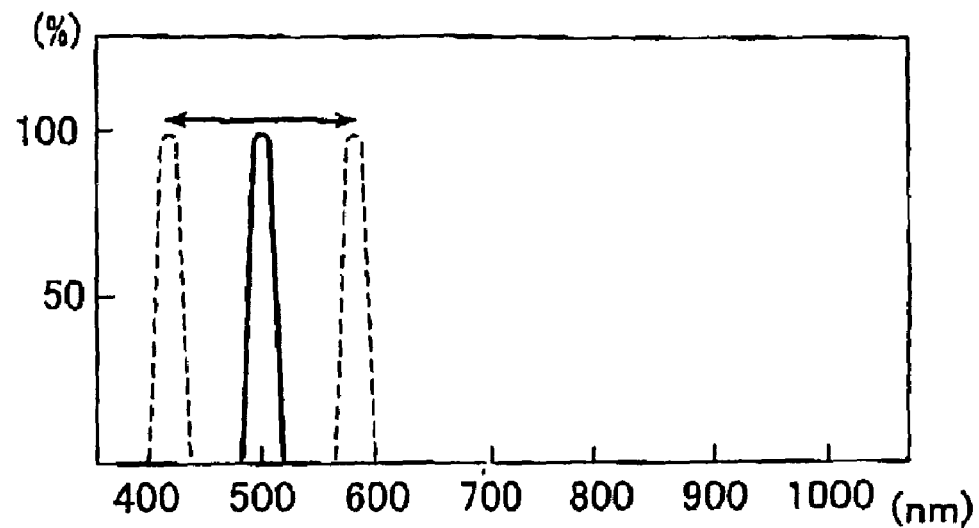
FIGS. 10(a) and 10(b) show the spectral transmittances of the small etalons ET1 and ET2, respectively, of Embodiment 3.
Figure 10B:
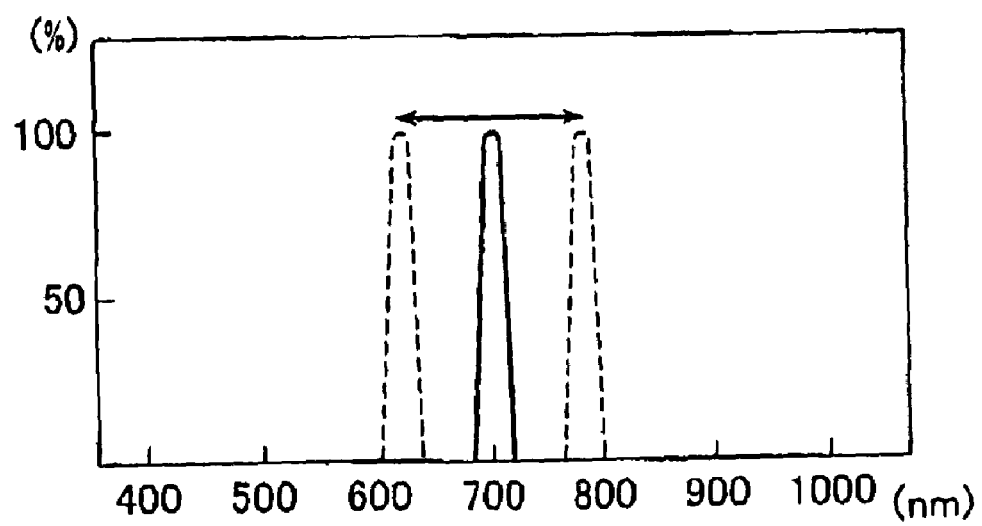

The fields of view θ of the four objective optical systems 12 overlap within the depth of field. Images of the subject 11 that are captured in the overlapped view field are formed in the four image pickup areas, respectively. For example, the small etalons 4I and 4II have a variable peak transmittance wavelength between 400 and 600 nm, as shown in FIG. 10(a), and the small etalons 4III and 4IV have a variable peak transmittance wavelength between 600 and 800 nm, as shown in FIG. 10(b). The air gap spacings of the small etalons 4I and 4II and the air gap spacings of the small etalons 4III and 4IV can be independently changed to select any of four different wavelengths between 400 nm and 800 nm that may be transmitted by the variable transmittance optical element for forming images.

Figure 12C:
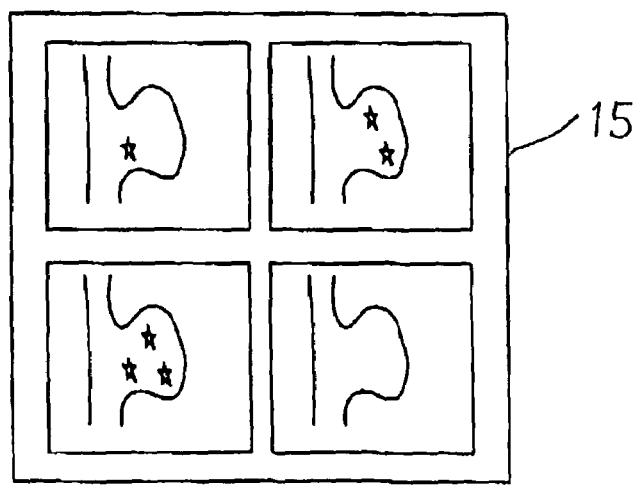

FIG. 12(c) shows an example of a display of images that may be captured by the endoscope imaging unit of the present embodiment. By setting the small etalons 4I, 4II, 4III, and 4IV for different air gap spacings, four different spectral data can be obtained for the same subject 11. The obtained data can be processed by an image processor (not illustrated) and displayed on the display screen 15 of a TV monitor, allowing for real-time spectral image diagnosis. This enables improved accuracy of diagnosis based on there being additional information available in the endoscope images, and saves endoscope examination time.

In the present embodiment, the small etalons 4I, 4II, 4III, and 4IV are used in separate areas for capturing images in four image pickup areas. Multiple small etalons can be provided for each image pickup area. Further, if no small etalon is provided for one of the image pickup areas, a color image of the subject 11 can be obtained in that image pickup area, thereby providing a color image along with spectral images obtained in narrow wavelength regions.

In the present embodiment, four objective lenses that exhibit the same optical performance are used, but some of these may be replaced with an objective lens exhibiting different optical performance. For example, a further detailed observation of the subject 11 is available by using an objective optical system that can come close to the subject 11 for close-up observation as a replacement objective optical system. In this case, by using an objective optical system wherein the depth of field at least partly overlaps that of the other objective lenses, one can ensure that focused images are obtainable even when the distal end of the endoscope is approaching very close to the subject 11, thereby facilitating operation of the endoscope.

Embodiment 5

Figure 13A:
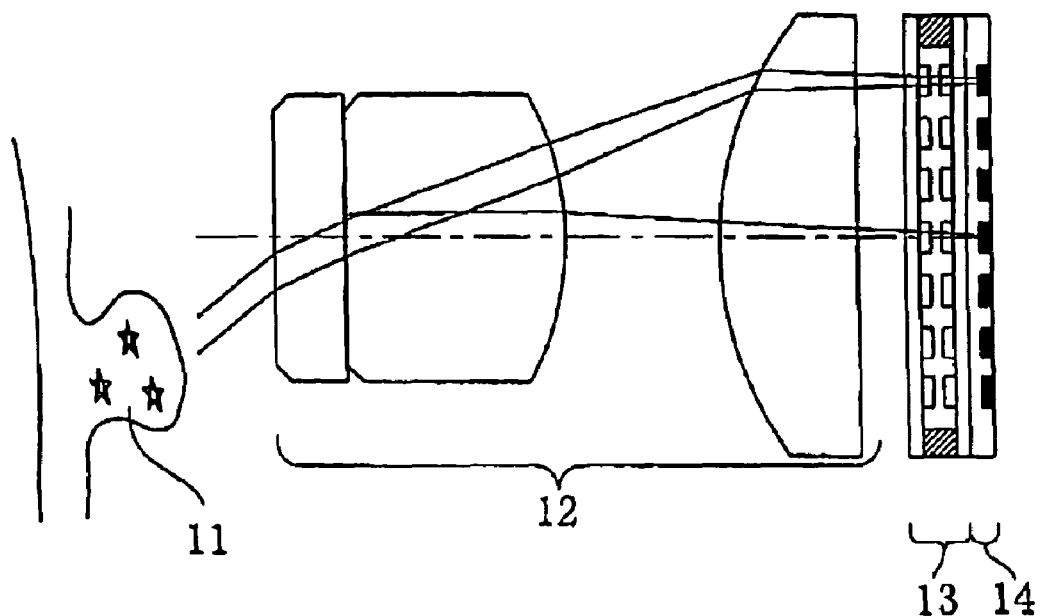
FIGS. 13(a) and 13(b) show the structure of an endoscope imaging unit according to Embodiment 5 of the present invention, with the variable transmittance optical element 13 in FIG. 13(a) having the structure as shown in FIGS. 7(a) and 7(b) and being positioned immediately before the image pickup surface. 14 of the image pickup device, and the variable transmittance optical element 13 in FIG. 13(b) having the structure as shown in FIGS. 8(a) and 8(b) and being positioned immediately before the image pickup surface 14 of the image pickup device.
Figure 13B:
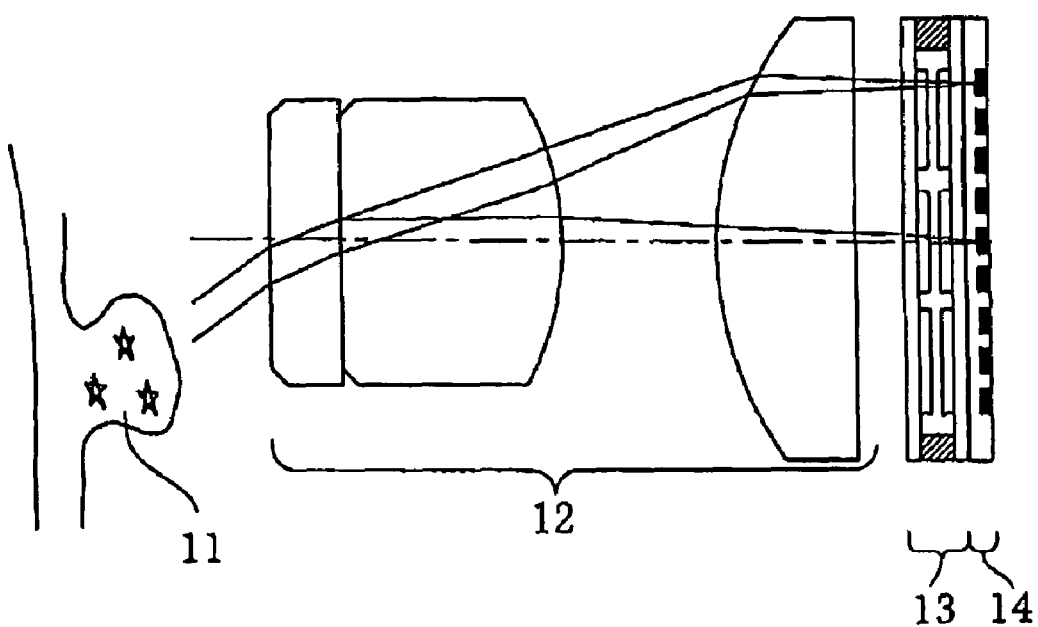

FIGS. 13(a) and 13(b) show the structure of an endoscope imaging unit according to Embodiment 5 of the present invention, with the variable transmittance optical element 13 in FIG. 13(a) having the structure as shown in FIGS. 7(a) and 7(b) and being positioned immediately before the image pickup surface 14 of the image pickup device, and the variable transmittance optical element 13 in FIG. 13(b) having the structure as shown in FIGS. 8(a) and 8(b) and being positioned immediately before the image pickup surface 14 of the image pickup device. In FIGS. 13(a) and 13(b) are shown a subject 11 (i.e., a portion of a living body), an objective lens 12, a variable transmittance optical element 13, and an image pickup surface 14 of an image pickup device such as a CCD. The objective lens 12 is a nearly telecentric optical system. Therefore, light enters the image pickup surface 14 of the image pickup device at nearly the same angle throughout the image pickup area. In this embodiment, the variable transmittance optical element 13 includes multiple microscopic mirrors that have an effective part that allows passage of a light beam received at a unit light receiving area that corresponds to an individual pixel of the image pickup device. The multiple microscopic mirrors are arranged in parallel on the facing surfaces of transparent substrates. The microscopic mirrors are formed by depositing reflective coatings on the substrates. A voltage is applied to piezoelectric elements that are provided between the transparent substrates so as to deform the piezoelectric elements. Consequently, at least one of the transparent substrates moves to change the mutual distance between the facing microscopic mirrors. The variable transmittance optical element 13 and the image pickup surface 14 of the image pickup device are positioned so that each microscopic mirror allows passage of a light beam entering an individual pixel.

In FIG. 13(b), the variable transmittance optical element 13 is placed immediately before the image pickup surface 14 of the image pickup device (i.e., the same positioning as in the variable transmittance optical element shown in FIGS. 8(a) and 8(b)). The variable transmittance optical element 13 includes multiple microscopic mirrors that have an effective part that allows passage of a light beam received at a unit light receiving area corresponding to multiple pixels of the image pickup device and are arranged in parallel on the facing surfaces of transparent substrates. The microscopic mirrors are formed by depositing reflective coatings on the transparent substrates. A voltage may be applied to a piezoelectric element, such as one that is provided between the transparent substrates, to deform the piezoelectric element. Consequently, at least one of the transparent substrates moves to change the mutual distance between the facing microscopic mirrors. The variable transmittance optical element 13 and the image pickup surface 14 of the image pickup device are positioned so that each microscopic mirror allows passage of a light beam entering multiple pixels. The part of the transparent substrates where no microscopic mirror is provided has a light-shielding means (not illustrated) such as a light-shielding mask.

A built-in drive unit (not shown) for the variable transmittance optical element 13 that is provided in the endoscope controls timing for changing the air gap spacings of the variable transmittance optical element 13. The timing for changing the air gap spacings of the variable transmittance optical element 13 is synchronized with the timing for illuminating the subject 11 or with the timing for reading image signals that have been acquired by the image pickup device.

Embodiment 6

Figure 14:
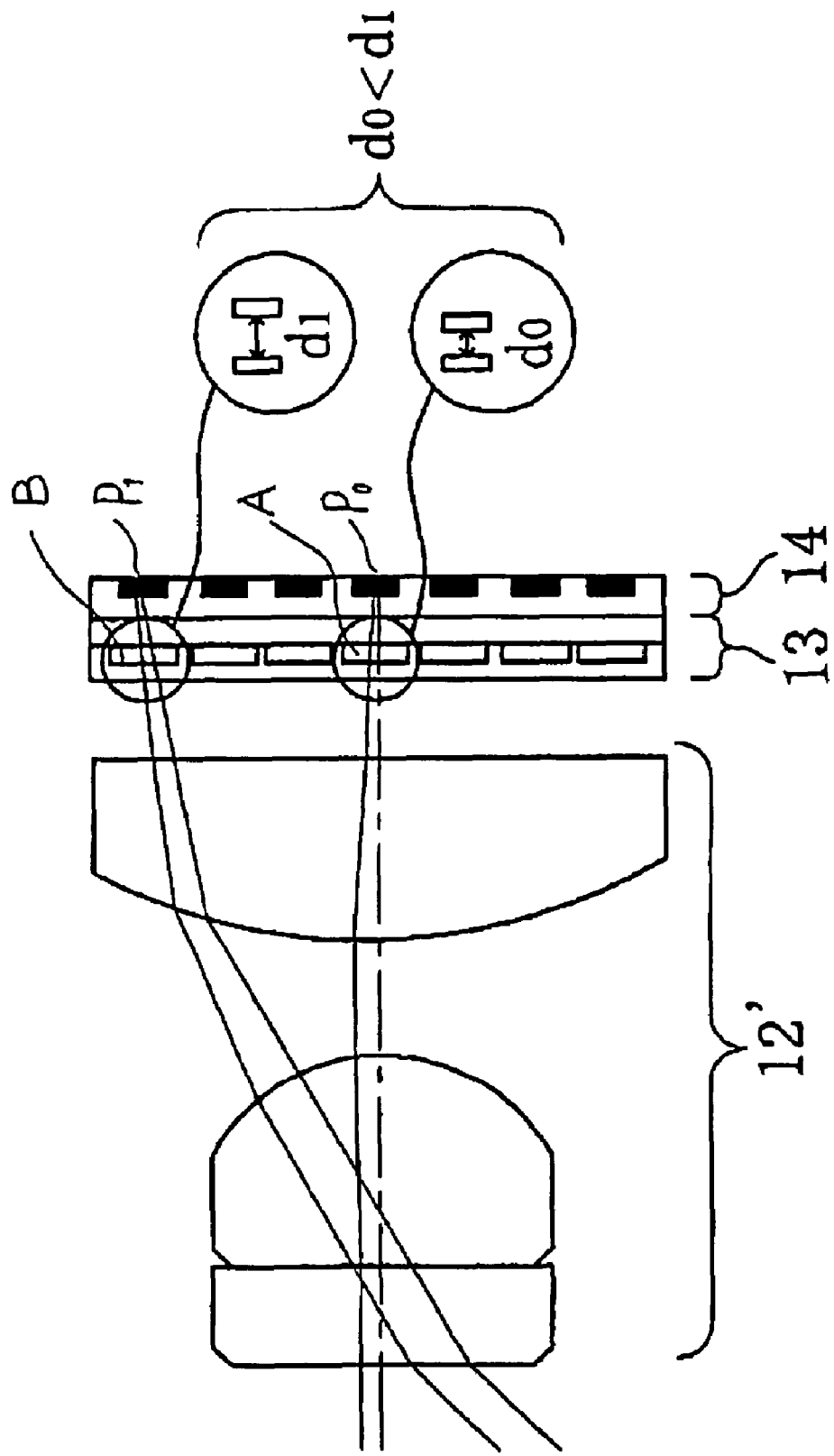
FIG. 14 shows the structure of an endoscope imaging unit according to Embodiment 6 of the present invention.

FIG. 14 shows the structure of an endoscope imaging unit according to Embodiment 6 of the present invention. More specifically, FIG. 14 shows an objective lens 12', a variable transmittance optical element 13, and an image pickup surface 14 of an image pickup device such as a CCD. A light beam from the objective lens 12' enters the image pickup surface 14 of the image pickup device at angles proportionally increasing with the image height on the image pickup surface of the image pickup device.

The variable transmittance optical element 13 has the same structure as in Embodiment 1 and includes multiple small etalons arranged on a plane facing the image pickup surface 14 of the image pickup device. $P_0$ is an imaging point on the optical axis and d0 is the air gap spacing of a small etalon A through which a light beam is incident onto the point $P_0$. $P_1$ is the maximum image height point on the image pickup surface 14 of the image pickup device, and d1 is the air gap spacing of a small etalon B through which a light beam is incident onto the point $P_1$.

As shown in FIG. 14, the incident angle of a light beam onto the small etalon B is larger than that of a light beam onto the small etalon A. It is generally known that the transmittance of an etalon for an oblique incident light beam is shifted to the shorter wavelength side as compared with the transmittance for a light beam that is incident parallel to the surface normal. It is further known that the transmittance of an etalon for an incident light beam is shifted to the longer wavelengths side as the air gap spacing is increased. In the endoscope imaging unit of the present embodiment, the small etalons at larger image height positions have wider air gap spacings in order to compensate for the transmittance shifts due to the incident angles of imaging light beams varying. Therefore, the relationship d0<d1 is always satisfied when the air gap spacings of the smaller etalons are changed.

Thus, in the imaging unit of the present embodiment having the above structure, the same wavelength component may be separated throughout the image pickup area despite the changing incident angles so as to obtain a specified, narrow band spectral image of a subject.

Embodiment 7

Figure 15:
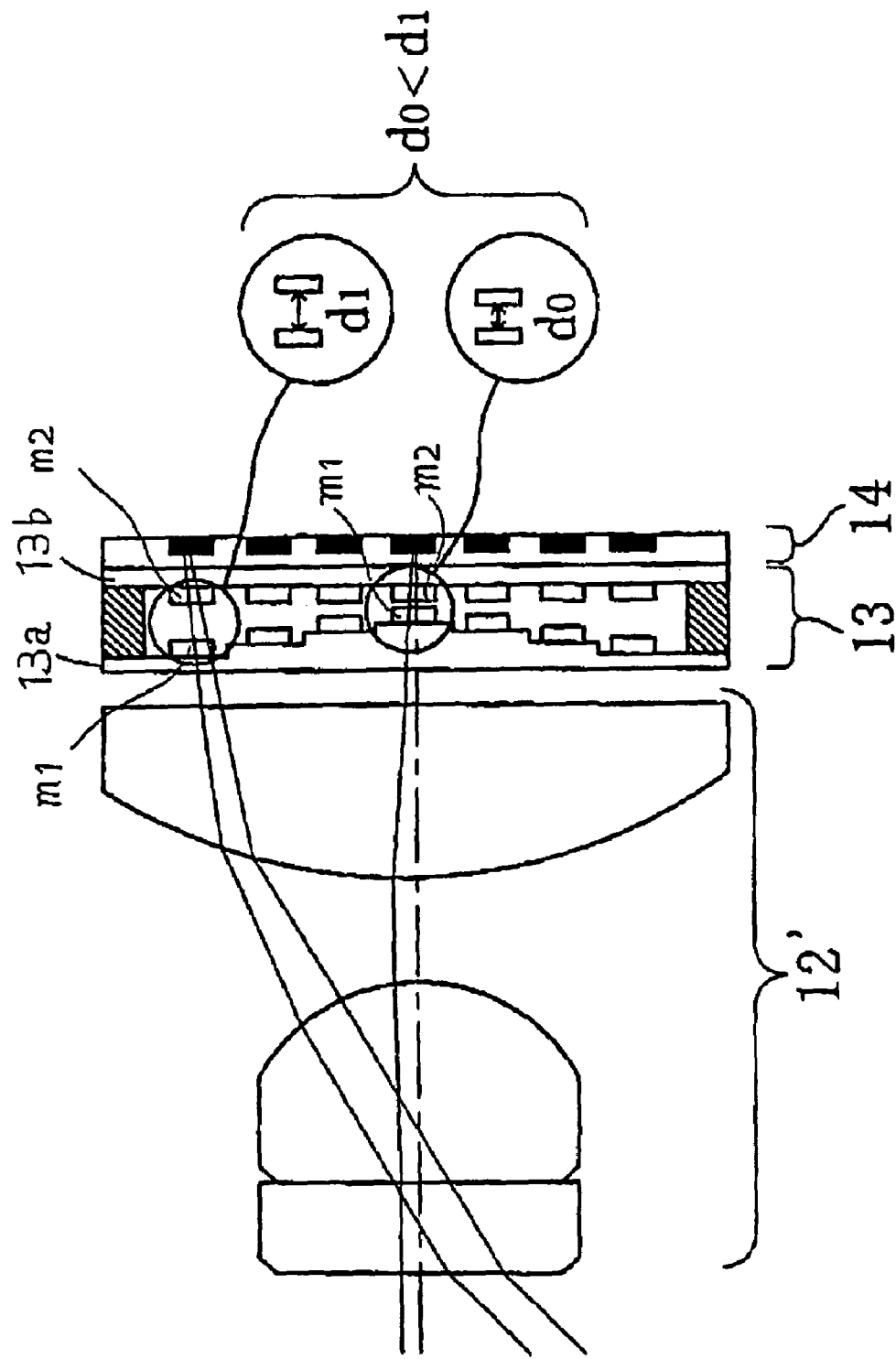
FIG. 15 shows the structure of an endoscope imaging unit according to Embodiment 7 of the present invention.
Figure 16:
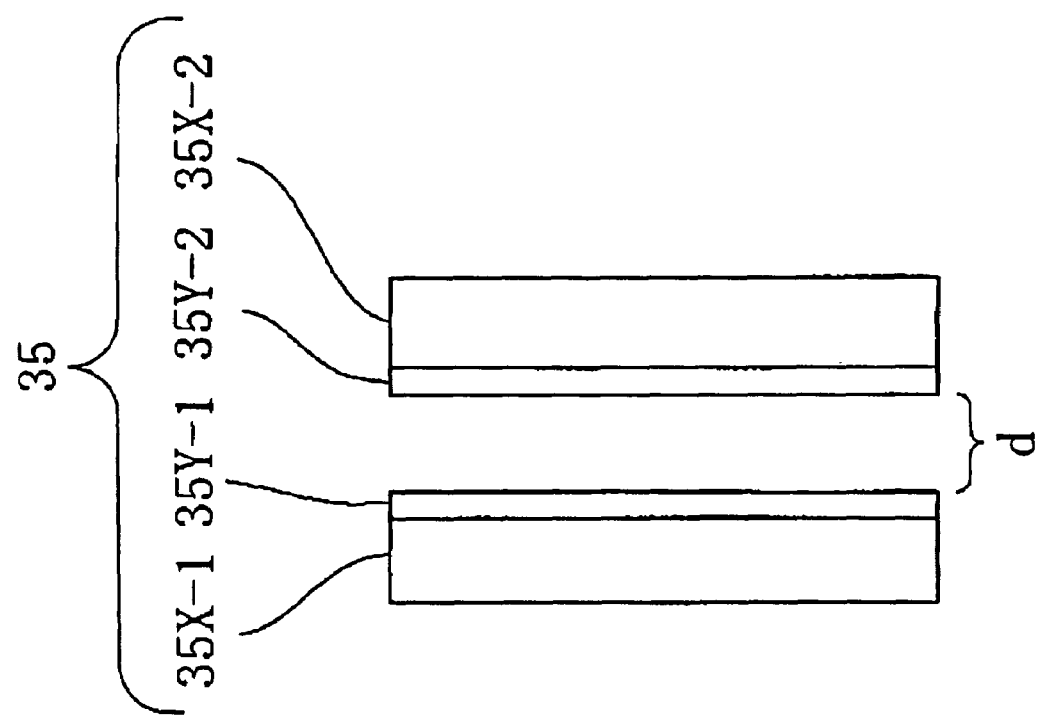
FIG. 16 shows the structure of a prior art variable transmittance optical element that uses a single etalon.
Figure 17:
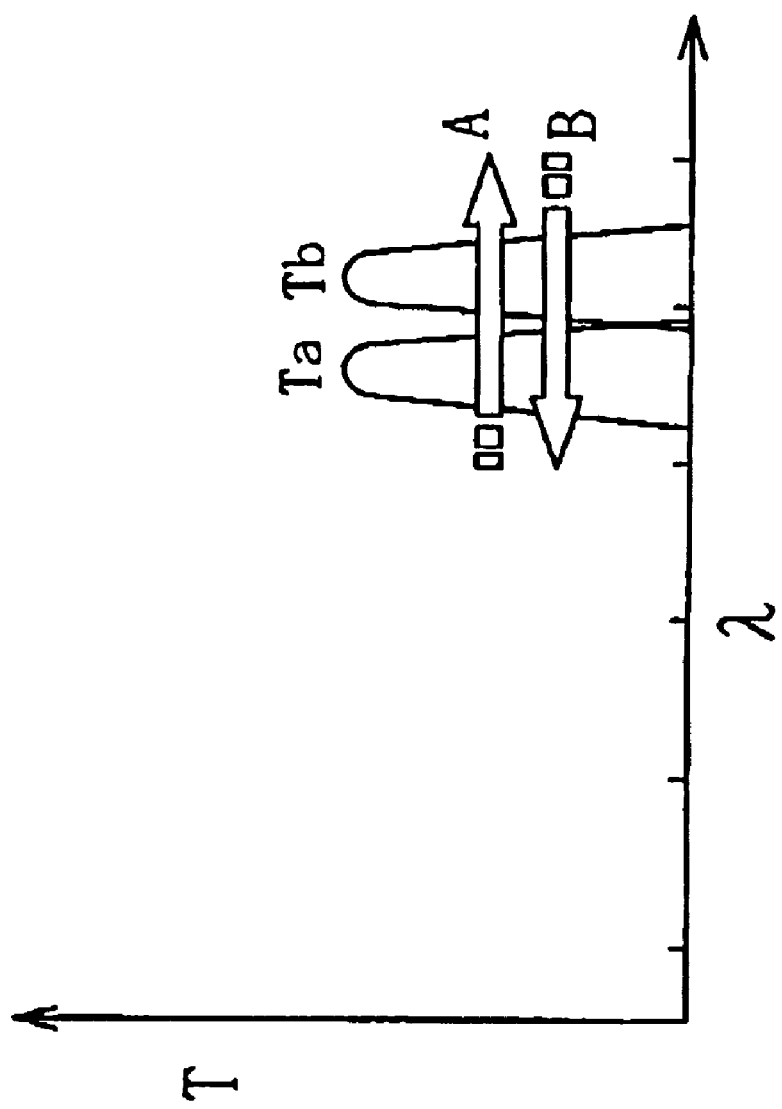
FIG. 17 shows the spectral transmittance, at two air gap spacings A and B, of the prior art variable transmittance optical element shown in FIG. 16.

FIG. 15 shows the structure of an endoscope imaging unit according to Embodiment 7 of the present invention. The endoscope imaging unit of Embodiment 7 is obtained by modifying the structure of the variable transmittance optical element 13 in the endoscope imaging unit of Embodiment 6. The variable transmittance optical element 13 of this embodiment includes a transparent substrate 13a of which one surface has a stepwise decreasing thickness from the center to the periphery, and a transparent substrate 13b having a uniform thickness from the center to the periphery. Microscopic mirrors m1 are formed on the stepped surfaces of the transparent substrate 13a. Facing those microscopic mirrors m1, microscopic mirrors m2 are formed on the surface of the substrate 13b. Therefore, the air gap spacings that are formed by the microscopic mirrors m1 and m2 increase as one proceeds from the optical axis center to the periphery of the variable transmittance optical element. With the variable transmittance optical element 13 having the above structure, the present embodiment has the same efficacy as the endoscope imaging pickup unit of Embodiment 6.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A variable transmittance optical element that is provided in an imaging optical system of an endoscope, said variable transmittance optical element comprising:

small etalons that have an effective part that allows passage of a light beam received at a unit light receiving area that corresponds to an individual pixel, or a plurality of pixels, of an image pickup device that is provided in the imaging optical system of the endoscope; each of said small etalons having facing surfaces that are arranged so as to be parallel to one another on a transparent substrate; and said transparent substrate and an image pickup surface of the image pickup device are positioned so that each of the small etalons allows passage of the light beam to said unit light receiving area.

2. The variable transmittance optical element according to claim 1, wherein:

said small etalons are formed by facing substrates having a size on the order of several µm, and a substrate that is farther away from the image pickup surface of the image pickup device has a larger effective part than a substrate that is closer to the image pickup surface of the image pickup device.

3. A variable transmittance optical element that is provided in the imaging optical system of an endoscope, wherein:

said variable transmittance optical element includes multiple microscopic mirrors that have an effective part that allows passage of a light beam that is received at a unit light receiving area corresponding to an individual pixel, or a plurality of pixels, of an image pickup device that is provided in the imaging optical system of the endoscope and said multiple microscopic mirrors are arranged on the facing surfaces of two transparent substrates; and at least one of the transparent substrates is moved so as to change the mutual distance between the facing microscopic mirrors.

4. The variable transmittance optical element according to claim 3, wherein:

the mutual distance between the facing microscopic mirrors increases from the center to the periphery of the variable transmittance optical element.

5. An endoscope imaging unit; wherein an objective lens and a variable transmittance optical element are provided;

said variable transmittance optical element includes small etalons that have an effective part that allows passage of a light beam that is received at a unit light receiving area that corresponds to an individual pixel, or a plurality of pixels, of an image pickup device that is provided in the imaging optical system of an endoscope, said small etalons being arranged on a transparent substrate; and said transparent substrate and an image pickup surface of the image pickup device are positioned so that each of the small etalons allows passage of the light beam to said unit light receiving area.

6. The endoscope imaging unit according to claim 5, wherein:

said small etalons include small etalons ET1 having a variable peak transmittance wavelength in the wavelength range of 400 nm-600 nm and small etalons ET2 having a variable peak transmittance wavelength in the wavelength range of 600 nm-800 nm; and images formed by pixels using light which has transmitted through small etalons ET1 and images formed by pixels using light which has transmitted through small etalons ET2 are separately obtained.

7. The endoscope imaging unit according to claim 5, wherein:

said image pickup surface of the image pickup device is divided into multiple image pickup areas;

each image pickup area is provided with an objective lens; and said small etalons are controlled for each image pickup area.

8. The endoscope imaging unit according to claim 7, wherein the fields of view of the objective lenses overlap.

9. The endoscope imaging unit according to claim 7, wherein:
of the multiple image pickup areas, at least one image pickup area is provided with light that has transmitted through small etalons ET1, each small etalon ET1 having a variable peak transmittance wavelength in the wavelength range of 400 nm-600 nm; and the other image pickup areas are provided with small etalons ET2, each small etalon ET2 having a variable peak transmittance wavelength in the wavelength range of 600 nm-800 nm; and images formed at the respective image pickup areas are separately obtained.

\* \* \* \* \*